(12) United States Patent
Li et al.

(10) Patent No.: US 9,216,953 B2
(45) Date of Patent: Dec. 22, 2015

(54) CHIRAL 2-ARYLPROPYL-2-SULFINAMIDE AND CHIRAL N-2-ARYLPROPYL-2-SULFINYLIMINES AND SYNTHESIS THEREOF

(71) Applicants: Guigen Li, Nanjing (CN); Suresh Pindi, Lubbock, TX (US)

(72) Inventors: Guigen Li, Nanjing (CN); Suresh Pindi, Lubbock, TX (US)

( * ) Notice: Subject to any disclaimer, the term of this patent is extended or adjusted under 35 U.S.C. 154(b) by 0 days.

(21) Appl. No.: 14/440,590

(22) PCT Filed: Nov. 15, 2012

(86) PCT No.: PCT/US2012/065336
§ 371 (c)(1),
(2) Date: May 4, 2015

(87) PCT Pub. No.: WO2014/070215
PCT Pub. Date: May 8, 2014

(65) Prior Publication Data
US 2015/0274654 A1      Oct. 1, 2015

Related U.S. Application Data

(60) Provisional application No. 61/721,499, filed on Nov. 2, 2012.

(51) Int. Cl.
*C07C 313/06* (2006.01)
*C07C 313/24* (2006.01)
*C07D 307/45* (2006.01)
*C07D 307/52* (2006.01)
*C07C 313/02* (2006.01)

(52) U.S. Cl.
CPC ............. *C07C 313/24* (2013.01); *C07C 313/02* (2013.01); *C07C 313/06* (2013.01); *C07D 307/45* (2013.01); *C07D 307/52* (2013.01)

(58) Field of Classification Search
USPC .................................. 564/102, 275, 270, 271
See application file for complete search history.

(56) References Cited

PUBLICATIONS

Cogan et al., Catalytic Asymmetric Oxidation of tert-Butyl Disulfide. Synthesis of tert-Butanesulfinamides, tert-Butyl Sulfoxides, and tert-Butanesulfinimines, 1998, Journal of the American Chemical Society, vol. 120, No. 32, 8011-8019.*

* cited by examiner

*Primary Examiner* — Kristin Vajda

(57) ABSTRACT

Provided herein are novel chiral sulfinamide and imine compounds. Also provided herein are methods of synthesizing novel chiral sulfinamide and imine compounds comprising simplified purification methods when compared to prior methods. The novel chiral sulfinamide and imine compounds are useful, for example, in the synthesis of complex natural products and pharmaceutical important compounds.

4 Claims, No Drawings

CHIRAL 2-ARYLPROPYL-2-SULFINAMIDE AND CHIRAL N-2-ARYLPROPYL-2-SULFINYLIMINES AND SYNTHESIS THEREOF

CROSS-REFERENCE TO RELATED APPLICATION

This application is a 371(c) National Stage Entry of International Patent Application No. PCT/US2012/065336, entitled "CHIRAL 2-ARYLPROPYL-2-SULFINAMIDE AND CHIRAL N-2-ARYLPROPYL-2-SULFINYLIMINES AND SYNTHESIS THEREOF" filed 15 Nov. 2012, which claims the benefit of, and priority to U.S. provisional patent application Ser. No. 61/721,499, entitled "DESIGN AND SYNTHESIS OF CHIRAL 2-ARYLPROPYL-2-SULFINAMIDE AND CHIRAL N-2-ARYLPROPYL-2-SULFINYLIMINES" filed 2 Nov. 2012, which is incorporated by reference herein in its entirety.

FIELD

Provided herein are novel chiral sulfinamide and imine compounds. Also provided herein are methods of synthesizing novel chiral sulfinamide and imine compounds comprising simplified purification methods when compared to prior methods. The novel chiral sulfinamide and imine compounds are useful, for example, in the synthesis of complex natural products and pharmaceutically important compounds.

BACKGROUND

Imine chemistry plays a pivotal role in producing biologically active amine compounds. F. A. Davis, P. Zhou, B. C. Chen, *Chem. Soc. Rev.* 1998, 27, 13-18). The asymmetric nucleophilic addition reaction on imines produces a wide variety of chiral amine containing moieties. F. A. Davis, B. Yang, *J. Am. Chem. Soc.* 2006, 127, 8938-8407; F. A. Davis, R. E. Reddy, J. M. Szewczyk, G. V. Reddy, P. S. Potonovo, H. Zhang, D. T. Reddy, P. Zhou, P. Carroll, *J. Org. Chem.* 1997, 62, 2555-2563; D. A. Cogan, G. C. Liu, K. J. Kim, B. J. Backes, J. A. Ellman, *J. Am. Chem. Soc.* 1998, 120, 8011-8019; D. A. Cogan, J. A. Ellman, *J. Am. Chem. Soc.* 1999, 121, 268-269; D. J. Weix, Y. L. Shi, J. A. Ellman, *J. Am. Chem. Soc.* 2005, 127, 1092-1093, X. Han, D. Krishnamurthy, P. Grover, Q. K. Fang, C. H. Senanayake, *J. Am. Chem. Soc.* 2002, 124, 7880-7881; J. G. Ruano, I. Fernandez, M. del P. Catalina, A. A. Cruz, *Tetrahedron Asymm.*, 1996, 7, 3407-3414; X. W. Sun, M. H. Xu, G. Q. Lin, *Org. Lett.* 2006, 8, 4979-4982; C. H. Zhao, L. Liu, D. Wang, Y. J. Chen, *Eur. J. Org. Chem.* 2006, 2977-2986; D. H. Hua, S. W. Miao, J. S. Chen, S. Iguchi, *J. Org. Chem.* 1991, 56, 4-6). For example, nucleophilic addition of boronates unto imines produces the essential precursor for the synthesis of bortezomib (Velcade), the first FDA approved proteasome inhibitor drug. Beenen, M. A.; An, C.; Ellman, J. A. *J. Am. Chem. Soc.* 2008, 130, 6910. Nucleophilic addition of cyanides unto imines produces natural and unnatural α-amino acids, and these are very useful building blocks for the synthesis of polypeptides. (R)-cetirizine dihydrochloride is used for the treatment of allergies, and it can be synthesized in high enantiopurity with the help of imine chemistry. Pflum, D. A.; Krishnamurthy, D.; Han, Z.; Wald, S. A.; Senanayake, C. H. *Tetrahedron Lett.* 2002, 43, 923. Aryl Grignard addition to imines is one of the key steps to synthesis of tubulin polymerization inhibitor (S)—N-acetylcolchinol. Besong, G.; Jarowicki, K.; Kocienski, P. J.; Sliwinski, E.; Boyle, F. T. *Org. Biomol. Chem.* 2006, 4, 2193. In addition, there are several pharmacologically and biologically important compounds containing amine functionalities, wherein imine chemistry provides easy access to synthesize key precursors, and as a result to achieve the synthesis of target molecules. Davis, F. A., Deng, J., *Org. Lett.* 2005, 7(4), 621; Pflum, D. A. et al., *Tetra. Lett.* 43 (2002) 923.

With this interest, chiral N-phosphonylimines were developed and utilized in several asymmetric nucleophilic addition reactions such as aza-Henry, aza-Darzen, etc. to achieve excellent diastereoselectivities. A. Kattuboina, P. Kaur, T. Ai, G. Li, *Chem. Biol. & Drug Design,* 2008, 71, 216; A. Kattuboina, G. Li, *Tetrahedron Lett.* 2008, 49, 1573.

Later, research was conducted on further simplifying the imine chemistry by means of easy purification methods. In this process, the Group Assistant Purification (GAP) concept was developed, in which the addition reaction products are purified by simple washing with minimum amounts of solvents such as pentane, hexanes, heptane, ethyl acetate, etc. or mixture of solvents, depending on the solubility nature of the impurities and side products. Kaur, P.; Nguyen, T.; Li, G. *Eur. J. Org. Chem.* 2009, 912; Han, J.; Ai, T.; Li, G. *Synthesis* 2008, 16, 2519; Han, J.; Chen, Z.-X.; Ai, T.; Li, G. *Chem. Biol. Drug Des.* 2009, 73, 203; Chen, Z.-X.; Ai, T.; Kaur, P.; Li, G. *Tetrahedron Lett.* 2009, 50, 1079; Ai, T.; Li, G. *Bioorg. Med. Chem. Lett.* 2009, 19, 3967; Kaur, P.; Shakya, G.; Sun, H.; Pan, Y.; Li, G. *Org. Biomol. Chem.* 2010, 8, 1091; Ai, T.; Han, J.; Chen, Z. X.; Li, G. *Chem. Biol. Drug. Des.* 2009, 73, 203; Kattuboina, A.; Kaur, P.; Ai, T.; Li, G. *Chem. Biol. Drug Des.* 2008, 71, 216; Ai, T.; Pindi, S.; Kattamuri, P. V.; Li, G. *Sci. China Series B: Chem.* 2010, 53, 125; Pindi, S.; Kaur, P.; Shakya, G.; Li, G. *Chem. Biol. Drug Design,* 2011, 75, 20.

SUMMARY

To further explore this novel concept, new N-protection groups have been developed to avoid traditional column chromatography and assist the GAP technique, which is more economic and environmental friendly. As part of this discovery, novel chiral N-2-phenylpropyl-2-sulfinylimines were synthesized.

The present disclosure, therefore, provides the design and synthesis of novel chiral 2-arylpropyl-2-sulfinamides and corresponding imines, which can be utilized to synthesize chiral amines. Also provided herein is a new methodology to synthesize 2-arylpropyl-2-sulfonamides from the corresponding thiosulfinates, utilizing an alternative nitrogen source. The new methodologies provide successful synthesis of 2-arylpropyl-2-sulfonamides where the aryl group containing thiosulfinates fail to produce sulfonamides with the traditional Li/liquid NH$_3$ method.

In certain embodiments, provided herein is a compound according to Formula Ia or Ib:

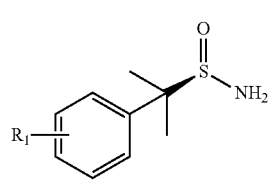

Formula (Ia)

Formula (Ib)

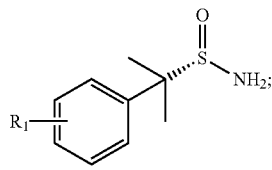

wherein each R₁ is independently hydrogen, alkyl or aryl.

In certain embodiments, provided herein is a compound according to formula IIIa or IIIb:

Formula (IIIa)

Formula (IIIb)

wherein each of R₁, R₂, and R₃ is independently hydrogen, alkyl or aryl.

In certain embodiments, provided herein is a method for preparing a compound of Formula Ia, the method comprising:
(a) reacting a compound of formula i2 in the presence of a compound of formula i3a to form a compound of formula i4a:

(b) reacting the compound of formula i4a in the presence of TBDMS-NH₂ to form a compound of formula i5a:

and (c) reacting the compound of formula i5a in the presence of TBAF to form the compound of formula Ia:

-continued

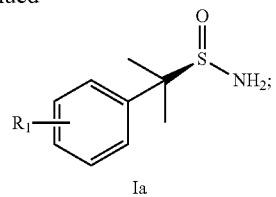

Ia wherein each $R_1$ is independently hydrogen, alkyl or aryl.

In certain embodiments, provided herein is a method for preparing a compound of formula Ib, the method comprising:
(a) reacting a compound of formula i2 in the presence of a compound of formula i3b to form a compound of formula i4b:

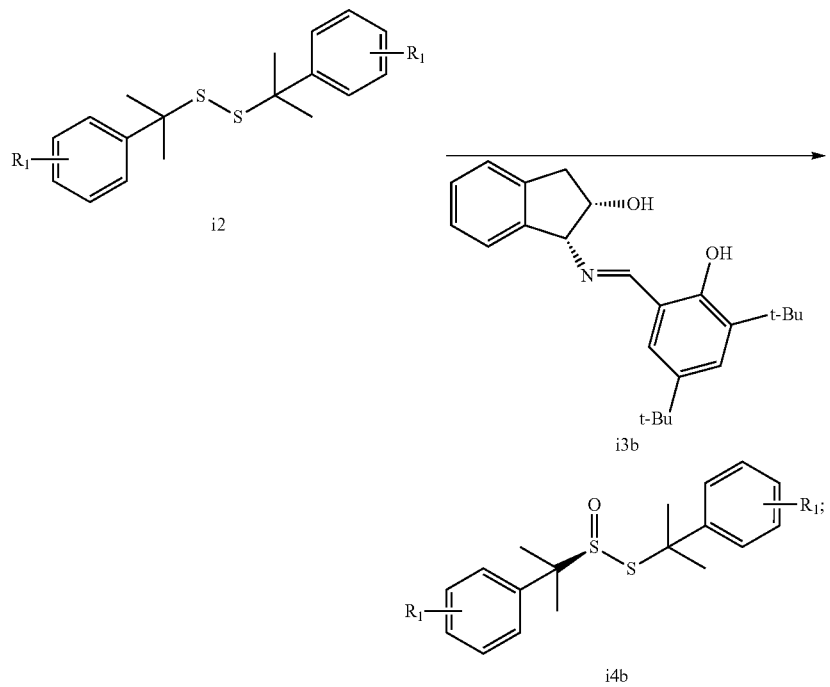

(b) reacting the compound of formula i4b in the presence of TBDMS-NH$_2$ to form a compound of formula i5b:

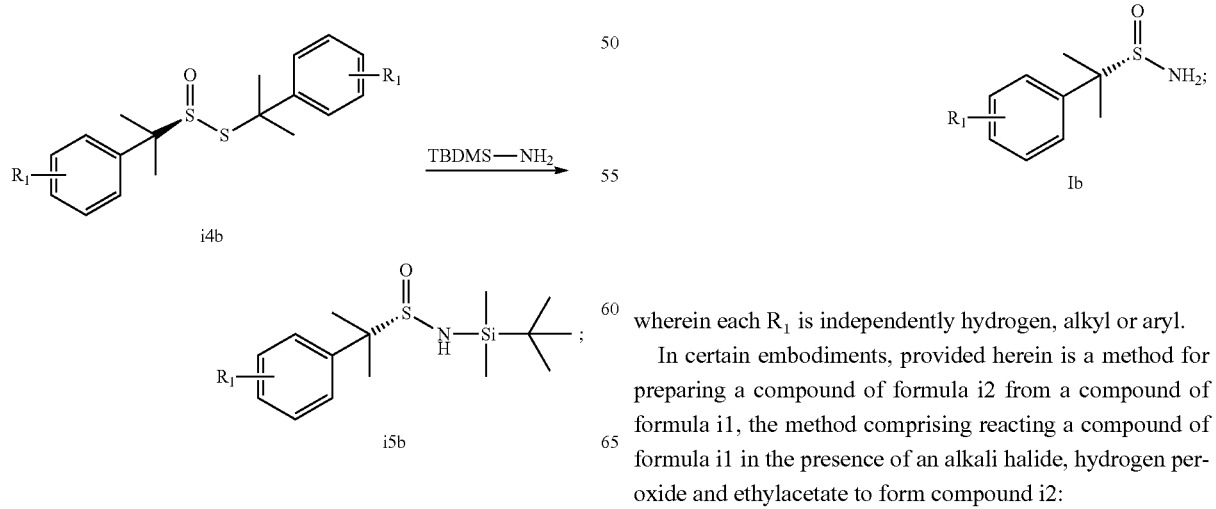

and (c) reacting the compound of formula i5b in the presence of TBAF to form the compound of formula Ib:

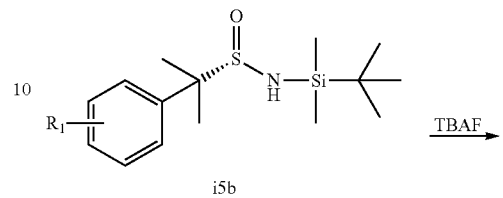

wherein each $R_1$ is independently hydrogen, alkyl or aryl.

In certain embodiments, provided herein is a method for preparing a compound of formula i2 from a compound of formula i1, the method comprising reacting a compound of formula i1 in the presence of an alkali halide, hydrogen peroxide and ethylacetate to form compound i2:

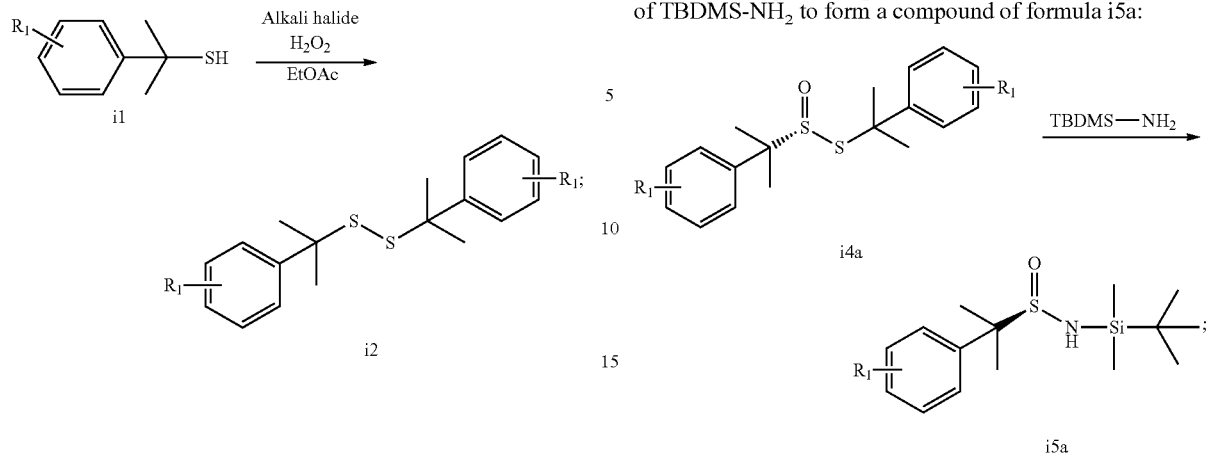

wherein each $R_1$ is independently hydrogen, alkyl or aryl.

In certain embodiments, provided herein is a method for preparing a compound of formula i5a, the method comprising: (a) reacting a compound of formula i2 in the presence of a compound of formula i3a to form a compound of formula i4a:

and (b) reacting the compound of formula i4a in the presence of TBDMS-NH$_2$ to form a compound of formula i5a:

wherein each $R_1$ is independently hydrogen, alkyl or aryl.

In certain embodiments, provided herein is a method for preparing a compound of formula i5b, the method comprising: (a) reacting a compound of formula i2 in the presence of a compound of formula i3b to form a compound of formula i4b:

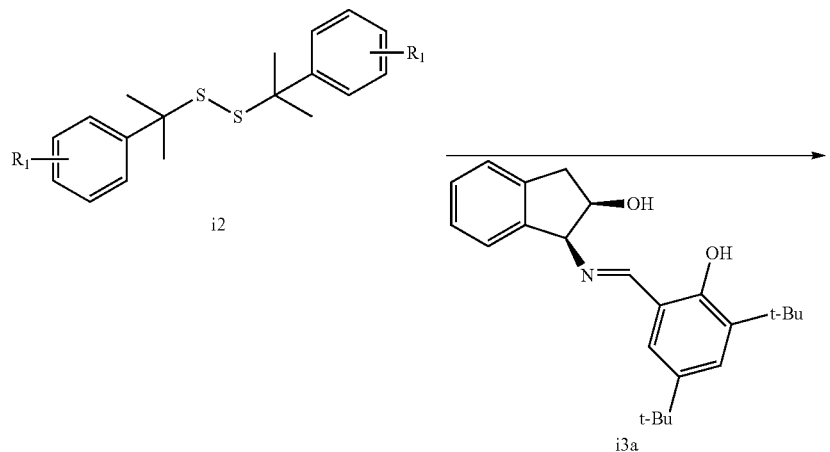

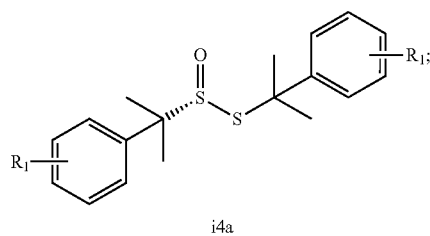

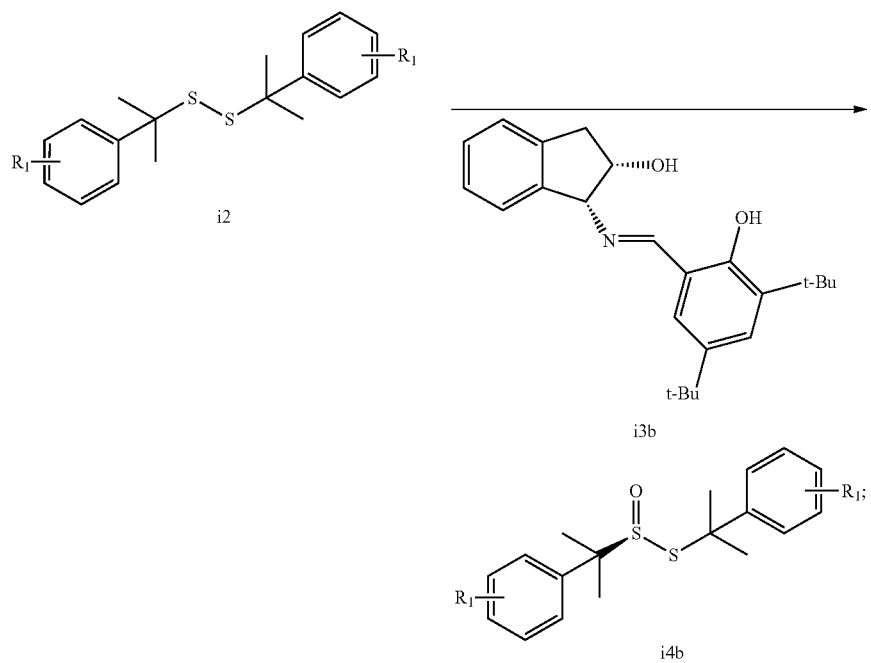

and (b) reacting the compound of formula i4b in the presence of TBDMS-NH$_2$ to form a compound of formula i5b:

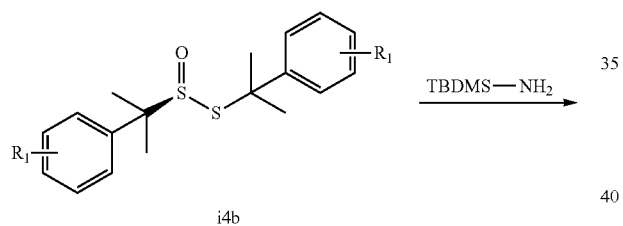

wherein each R$_1$ is independently hydrogen, alkyl or aryl.

In certain embodiments, provided here is a method for the preparation of a compound of formula IIIa, the method comprising reacting a compound of formula Ia with a compound of formula i6 to form a compound of formula IIIa:

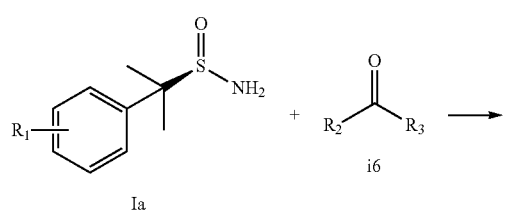

-continued

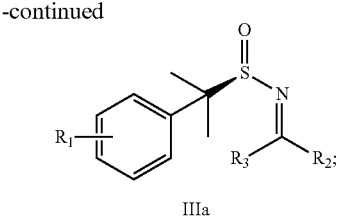

wherein each of R$_1$, R$_2$, and R$_3$ is independently hydrogen, alkyl or aryl.

In certain embodiments, provided herein is a method for the preparation of a compound of formula IIIb, the method comprising reacting a compound of formula Ib with a compound of formula i6 to form a compound of formula IIIb:

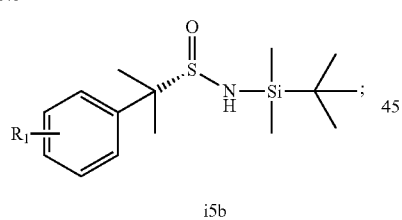

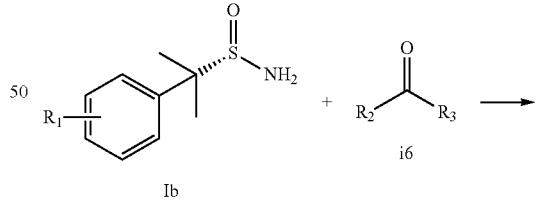

wherein each of R$_1$, R$_2$, and R$_3$ is independently hydrogen, alkyl or aryl.

The sulfinylimines described herein are useful, for example, in the chiral synthesis of Cetirizine using the method of Pflum et al. See, Pflum, D. A. et al., *Tetra. Lett.* 43 (2002) 923. The sulfinylimines described herein are also useful, for example, in the chiral synthesis of Agelastatin A. using the method of Davis and Deng. See, Davis, F. A., Deng, J., *Org. Lett.* 2005, 7(4), 621.

DESCRIPTION OF EXEMPLARY EMBODIMENTS

Provided herein are novel chiral sulfinamide and imine compounds. Also provided herein are methods of synthesizing novel chiral sulfinamide and imine compounds comprising simplified purification methods when compared to prior methods. The novel chiral sulfinamide and imine compounds are useful, for example, in the synthesis of complex natural products and pharmaceutical important compounds.

DEFINITIONS

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl", as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. In certain embodiments, the alkyl group is selected from the group consisting of methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl. The term includes both substituted and unsubstituted alkyl groups, including halogenated alkyl groups. In certain embodiments, the alkyl group is a fluorinated alkyl group. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl", as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties.

The term "cycloalkyl", as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl.

The term "cycloalkenyl", as used herein, unless otherwise specified, refers to an unsaturated cyclic hydrocarbon. In certain embodiments, cycloalkenyl refers to mono- or multi- cyclic ring systems that include at least one double bond. In certain embodiments, the cycloalkenyl group may be a bridged, non-bridged, and/or a fused bicyclic group. In certain embodiments, the cycloalkyl group includes three to ten carbon atoms, i.e., $C_3$ to $C_{10}$ cycloalkyl. In some embodiments, the cycloalkenyl has from 3 to 7 ($C_{3-10}$), or from 4 to 7 ($C_{3-7}$) carbon atoms.

"Alkylene" refers to divalent saturated aliphatic hydrocarbon groups particularly having from one to eleven carbon atoms which can be straight-chained or branched. In certain embodiments, the alkylene group contains 1 to 10 carbon atoms. The term includes both substituted and unsubstituted moieties. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" refers to monovalent olefinically unsaturated hydrocarbon groups, in certain embodiment, having up to about 11 carbon atoms, from 2 to 8 carbon atoms, or from 2 to 6 carbon atoms, which can be straight-chained or branched and having at least 1 or from 1 to 2 sites of olefinic unsaturation. The term includes both substituted and unsubstituted moieties. Exemplary alkenyl groups include ethenyl (i.e., vinyl, or —$CH=CH_2$), n-propenyl (—$CH_2CH=CH_2$), isopropenyl (—$C(CH_3)=CH_2$), and the like.

"Alkenylene" refers to divalent olefinically unsaturated hydrocarbon groups, in certain embodiments, having up to about 11 carbon atoms or from 2 to 6 carbon atoms which can be straight-chained or branched and having at least 1 or from 1 to 2 sites of olefinic unsaturation. This term is exemplified by groups such as ethenylene (—$CH=CH$—), the propenylene isomers (e.g., —$CH=CHCH_2$— and —$C(CH_3)=CH$— and —$CH=C(CH_3)$—) and the like.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—$C\equiv CH$), propargyl (—$CH_2C\equiv CH$), and the like.

The term "aryl", as used herein, and unless otherwise specified, refers to a cyclic aromatic hydrocarbon. In certain embodiments, aryl is furanyl, pyridinyl, phenyl, biphenyl, or naphthyl. The term includes both substituted and unsubstituted moieties. An aryl group can be substituted with any described moiety, including, but not limited to, one or more moieties selected from the group consisting of halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

"Alkoxy" refers to the group —OR' where R' is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Amino" refers to the radical —$NH_2$.

"Carboxyl" or "carboxy" refers to the radical —C(O)OH.

The term "alkylamino" or "arylamino" refers to an amino group that has one or two alkyl or aryl substituents, respectively. In certain embodiments, the alkyl substituent is lower alkyl. In another embodiment, the alkyl or lower alkyl is unsubstituted.

"Halogen" or "halo" refers to chloro, bromo, fluoro or iodo.

"Monoalkylamino" refers to the group alkyl-NR'—, wherein R' is selected from hydrogen and alkyl or cycloalkyl.

"Thioalkoxy" refers to the group —SR' where R' is alkyl or cycloalkyl.

The term "heterocyclyl" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "heteroaryl" refers to refers to a monovalent monocyclic aromatic group and/or multicyclic aromatic group that contain at least one aromatic ring, wherein at least one aromatic ring contains one or more heteroatoms independently selected from O, S, and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "alkylaryl" refers to an aryl group with an alkyl substituent. The term "aralkyl" or "arylalkyl" includes an alkyl group with an aryl substituent.

The term "alkylheterocyclyl" refers to a heterocyclyl group with an alkyl substituent. The term alkylheterocyclyl includes an alkyl group with a heterocyclyl substituent.

The term "alkylheteroaryl" refers to a heteroaryl group with an alkyl substituent. The term alkylheteroaryl includes an alkyl group with a heteroaryl substituent.

The term "protecting group" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "acyl" or "O-linked ester" refers to a group of the formula C(O)R', wherein R' is alkyl or cycloalkyl (including lower alkyl), carboxylate reside of amino acid, aryl including phenyl, alkaryl, arylalkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or arylalkyl sulphonyl including methanesulfonyl, the mono, di or triphosphate ester, trityl or monomethoxytrityl, substituted benzyl, alkaryl, arylalkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclpropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2, 2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoroheptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, 0-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "substantially free of" or "substantially in the absence of" with respect to a composition refers to a composition that includes at least 85% or 90% by weight, in certain embodiments 95%, 98%, 99% or 100% by weight, of a designated enantiomer of a compound. In certain embodiments, in the methods and compounds provided herein, the compounds are substantially free of enantiomers.

Similarly, the term "isolated" with respect to a composition refers to a composition that includes at least 85%, 90%, 95%, 98%, 99% or 100% by weight, of a compound, the remainder comprising other chemical species or enantiomers.

Similarly, the term "diastereomerically pure" with respect to a compound refers to a compound that includes at least 85% or 90% by weight, in certain embodiments 95%, 98%, 99% or 100% by weight of the designated diastereomer.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen", the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "cycloalkenyl," "alkynyl," "aryl," "alkoxy," "alkoxycarbonyl," "amino," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise deuterium at one or more positions where hydrogen atoms are present, and wherein the deuterium composition of the atom or atoms is other than the natural isotopic composition.

Also as used herein, "alkyl," "cyclo alkyl," "alkenyl," "cycloalkenyl," "alkynyl," "aryl," "alkoxy," "alkoxycarbonyl," "carboxyl," "alkylamino," "arylamino," "thioalkyoxy," "heterocyclyl," "heteroaryl," "alkylheterocyclyl," "alkylheteroaryl," "acyl," "aralkyl," "alkaryl," "purine," "pyrimidine," "carboxyl" and "amino acid" groups optionally comprise carbon-13 at an amount other than the natural isotopic composition.

The term "protected", as used herein and unless specified otherwise, refers to a group that is added to an oxygen, nitrogen or phosphorus atom to prevent its further reaction or for other purposes. A wide variety of oxygen, nitrogen and phosphorus protecting groups are known to those skilled in the art of organic synthesis.

Examples of suitable protecting groups include, but not limited to, benzoyl; substituted or unsubstituted alkyl groups, substituted or unsubstituted aryl groups, substituted or unsubstituted silyl groups; substituted or unsubstituted aromatic or aliphatic esters, such as, for example, aromatic groups like benzoyl, toluoyls (e.g. p-toluoyl), nitrobenzoyl, chlorobenzoyl; ether groups such as, for example, —C—O-aralkyl, —C—O-alkyl, or —C—O-aryl; and aliphatic groups like acyl or acetyl groups, including any substituted or unsubstituted aromatic or aliphatic acyl, —(C=O)-aralkyl, —(C=O)-alkyl, or —(C=O)-aryl; wherein the aromatic or aliphatic moiety of the acyl group can be straight-chained or branched; all of which may be further optionally substituted by groups not affected by the reactions comprising the improved synthesis (see Greene et al., *Protective Groups in Organic Synthesis*, John Wiley and Sons, 2nd Edition, 1991). For example, in one embodiment of the invention, the protecting groups are substituted by groups not affected by the reducing agent of choice, such as Red-Al. For the use of ethers as protective groups, attention is directed to U.S. Pat. No. 6,229,008 to Saischek et al., herein incorporated by reference, wherein it is reported that the use of an ether as a protective group may offer significant advantages for stability toward reagents and process conditions. This affords an ultimate advantage for separation, isolation, and purification of the desired product and thus, on the product's percent yield.

"Derivative," "analog," "chemical derivative," "derivatizing," and similar terms are given their ordinary meanings as well-known in the fields of chemistry, biochemistry, and/or biology. A derivative may be any chemical substance structurally related to another chemical substance and at least theoretically derivable from it. An analog may be a chemical or biological species that is similar enough to a parent species that it may substitute for the parent species in at least one set of chemical or biochemical interactions.

Synthetic Methods

In certain embodiments, provided herein is a method for preparing a compound of Formula Ia, the method comprising: (a) reacting a compound of formula i2 in the presence of a compound of formula i3a to form a compound of formula i4a:

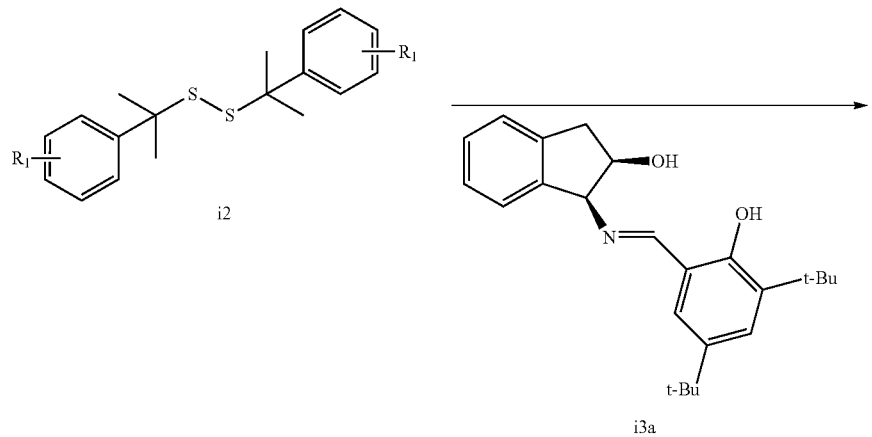

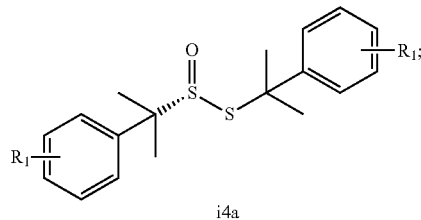

(b) reacting the compound of formula i4a in the presence of TBDMS-NH₂ to form a compound of formula i5a:

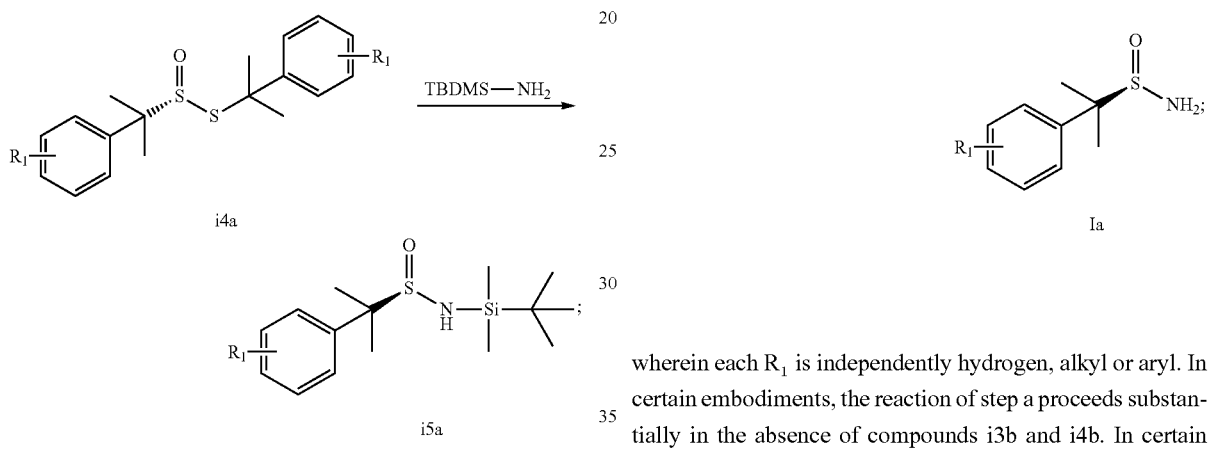

and (c) reacting the compound of formula i5a in the presence of TBAF to form the compound of formula Ia:

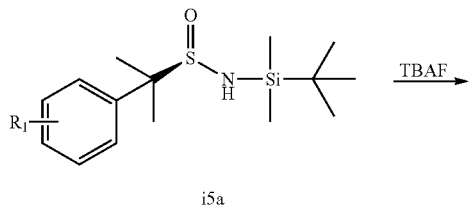

wherein each $R_1$ is independently hydrogen, alkyl or aryl. In certain embodiments, the reaction of step a proceeds substantially in the absence of compounds i3b and i4b. In certain embodiments, the reaction of step b proceeds substantially in the absence of compounds i4b and i5b. In certain embodiments, the reaction of step c proceeds substantially in the absence of compounds i5b and Ib.

In certain embodiments, provided herein is a method for preparing a compound of Formula Ib, the method comprising:
(a) reacting a compound of formula i2 in the presence of a compound of formula i3b to form a compound of formula i4b:

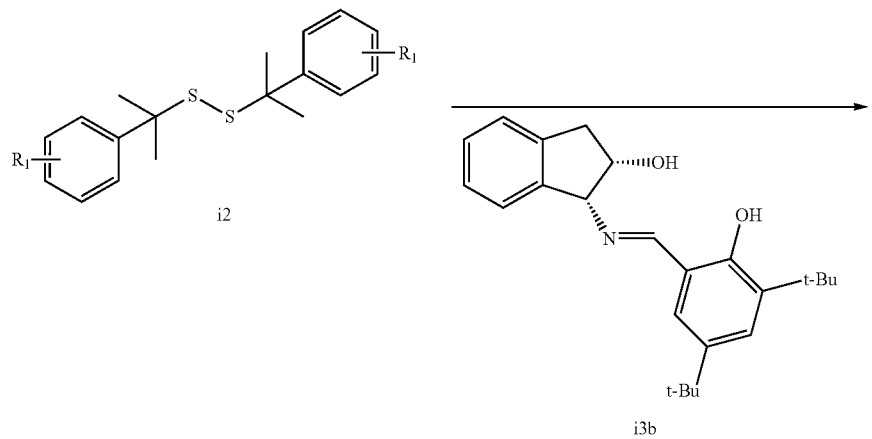

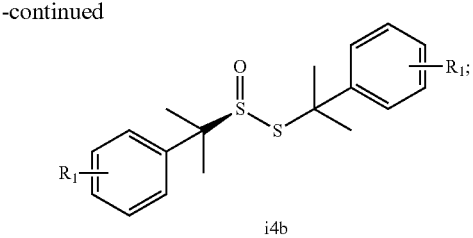

i4b (b) reacting the compound of formula i4b in the presence of TBDMS-NH$_2$ to form a compound of formula i5b:

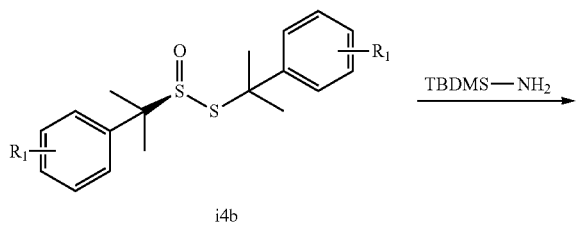

and (c) reacting the compound of formula i5b in the presence of TBAF to form the compound of formula Ib:

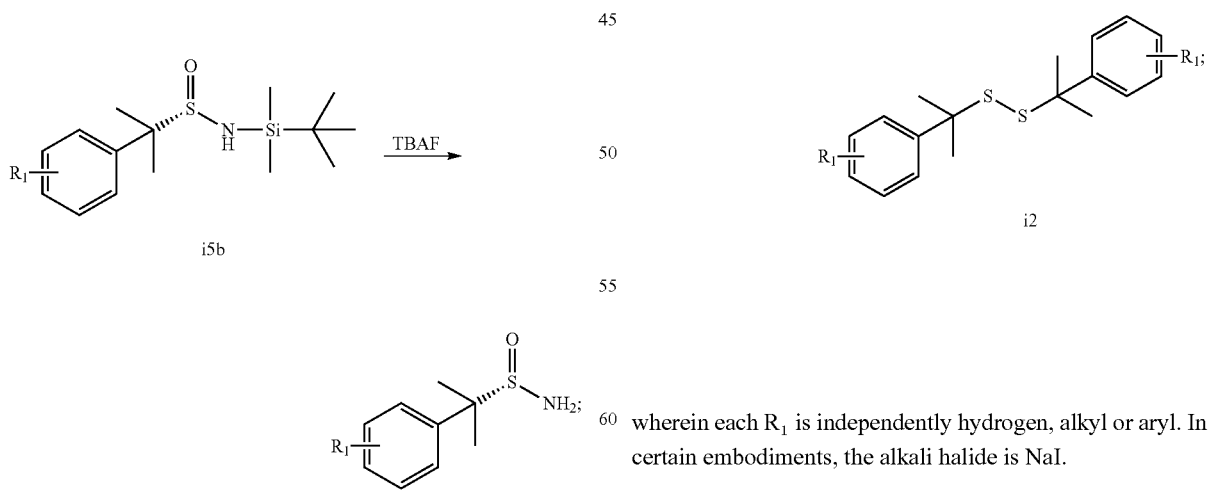

wherein each R$_1$ is independently hydrogen, alkyl or aryl.

In certain embodiments, the reaction of step a proceeds substantially in the absence of compounds i3a and i4a. In certain embodiments, the reaction of step b proceeds substantially in the absence of compounds i4a and i5a. In certain embodiments, the reaction of step c proceeds substantially in the absence of compounds i5a and Ia.

In certain embodiments, a method for preparing a compound of formula i2 from a compound of formula i1 is provided, the method comprising reacting a compound of formula i1 in the presence of an alkali halide, hydrogen peroxide and ethylacetate to form compound i2:

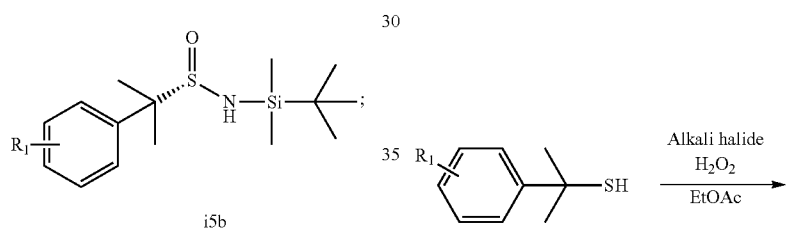

wherein each R$_1$ is independently hydrogen, alkyl or aryl. In certain embodiments, the alkali halide is NaI.

In certain embodiments, a method for preparing a compound of formula i5a is provided, the method comprising: (a) reacting a compound of formula i2 in the presence of a compound of formula i3a to form a compound of formula i4a:

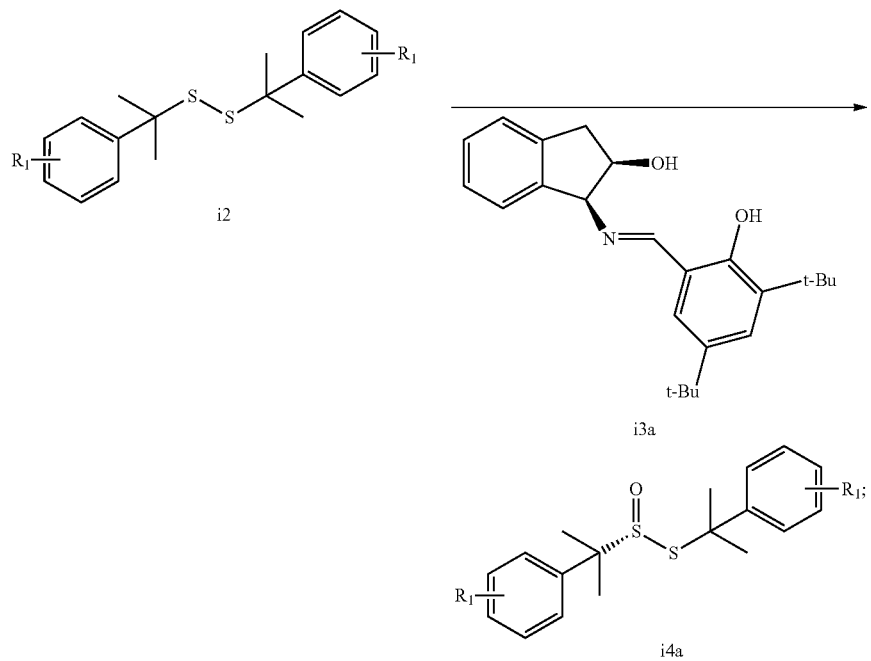

i2 i3a i4a and (b) reacting the compound of formula i4a in the presence of TBDMS-NH$_2$ to form a compound of formula i5a:

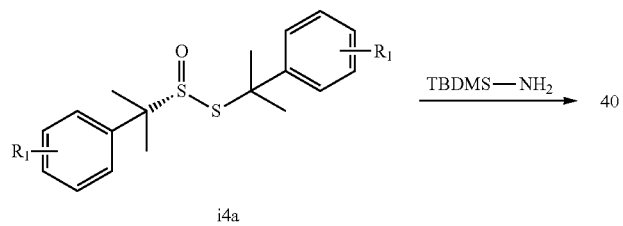

i4a

-continued i5a wherein each R$_1$ is independently hydrogen, alkyl or aryl. In certain embodiments, the reaction of step a proceeds substantially in the absence of compounds i3b and i4b. In certain embodiments, the reaction of step b proceeds substantially in the absence of compounds i4b and i5b.

In certain embodiments, a method for preparing a compound of formula i5b is provided, the method comprising: (a) reacting a compound of formula i2 in the presence of a compound of formula i3b to form a compound of formula i4b:

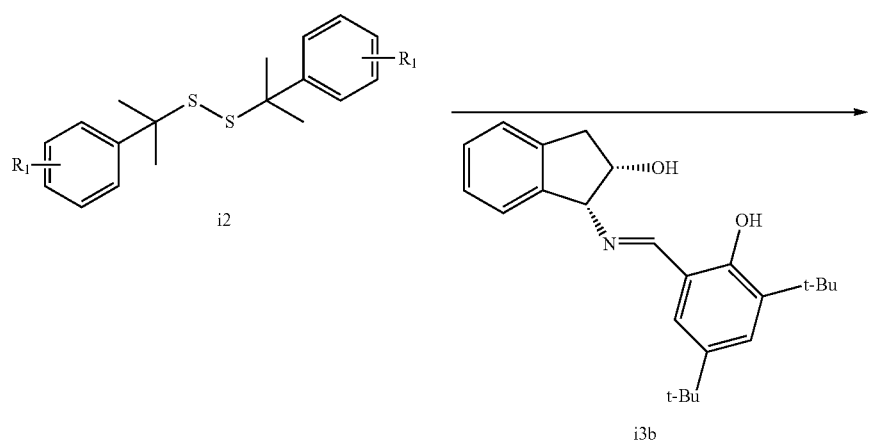

i2 i3b

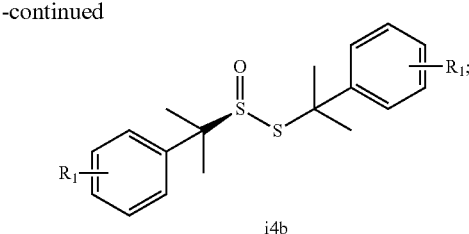

and (b) reacting the compound of formula i4b in the presence of TBDMS-NH$_2$ to form a compound of formula i5b:

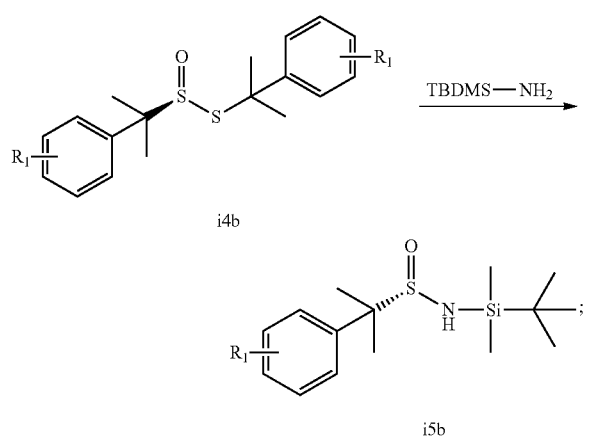

wherein each R$_1$ is independently hydrogen, alkyl or aryl. In certain embodiments, the reaction of step (a) proceeds substantially in the absence of compounds i3a and i4a. In certain embodiments, the reaction of step (b) proceeds substantially in the absence of compounds i4a and i5a.

In certain embodiments of the methods described herein, each R$_1$ is independently alkyl or aryl. In certain embodiments of the methods described herein, each R$_1$ is independently C$_4$-C$_{14}$ aryl. In certain embodiments of the methods described herein, each R$_1$ is independently C$_4$-C$_{10}$ aryl. In certain embodiments of the methods described herein, each R$_1$ is independently C$_4$-C$_{14}$ heteroaryl. In certain embodiments of the methods described herein, R$_1$ is independently C$_4$-C$_{10}$ heteroaryl. In certain embodiments of the methods described herein, each R$_1$ is independently furanyl, pyridinyl, phenyl, biphenyl, or naphthyl.

In certain embodiments of the methods described herein, each R$_1$ is independently lower alkyl. In certain embodiments of the methods described herein, each R$_1$ is independently C$_1$-C$_{20}$ alkyl. In certain embodiments of the methods described herein, each R$_1$ is independently C$_1$-C$_{10}$ alkyl. In certain embodiments of the methods described herein, each R$_1$ is independently C$_1$-C$_5$ alkyl.

In certain embodiments of the methods described herein, each R$_1$ is independently hydrogen, methyl, or isopropyl. In certain embodiments of the methods described herein, each R$_1$ is independently methyl or isopropyl. In certain embodiments of the methods described herein, wherein each R$_1$ is methyl. In certain embodiments of the methods described herein, R$_1$ is isopropyl. In certain embodiments of the methods described herein, each R$_1$ is hydrogen.

In certain embodiments, provided herein is a method for the preparation of a compound of formula IIIa, the method comprising reacting a compound of formula Ia with a compound of formula i6 to form a compound of formula IIIa:

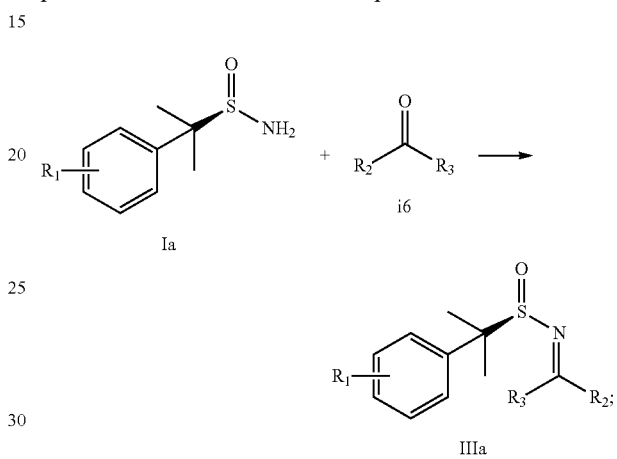

wherein each of R$_1$, R$_2$, and R$_3$ is independently hydrogen, alkyl or aryl. In certain embodiments of the above method, the reaction proceeds substantially in the absence of compound Ib.

In certain embodiments, provided herein is a method for the preparation of a compound of formula IIIb, the method comprising reacting a compound of formula Ib with a compound of formula i6 to form a compound of formula IIIb:

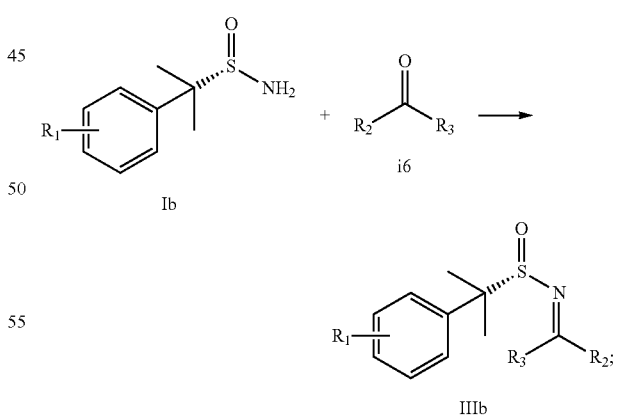

wherein each of R$_1$, R$_2$, and R$_3$ is independently hydrogen, alkyl or aryl. In certain embodiments of the above method, the reaction proceeds substantially in the absence of compound Ia.

In certain embodiments of the methods described above, each R$_1$ is independently alkyl or aryl. In certain embodiments of the methods described above, each R$_1$ is independently $C_4$-$C_{14}$ aryl. In certain embodiments of the methods described above, each $R_1$ is independently $C_4$-$C_{10}$ aryl. In certain embodiments of the methods described above, each $R_1$ is independently $C_4$-$C_{14}$ heteroaryl. In certain embodiments of the methods described above, each $R_1$ is independently $C_4$-$C_{10}$ heteroaryl. In certain embodiments of the methods described above, each $R_1$ is independently furanyl, pyridinyl, phenyl, biphenyl, or naphthyl.

In certain embodiments of the methods described above, each $R_1$ is independently lower alkyl. In certain embodiments of the methods described above, each $R_1$ is independently $C_1$-$C_{20}$ alkyl. In certain embodiments of the methods described above, each $R_1$ is independently $C_1$-$C_{10}$ alkyl. In certain embodiments of the methods described above, each $R_1$ is independently $C_1$-$C_5$ alkyl. In certain embodiments of the methods described above, each $R_1$ is independently hydrogen, methyl, or isopropyl. In certain embodiments of the methods described above, each $R_1$ is independently methyl or isopropyl. In certain embodiments of the methods described above, each $R_1$ is methyl. In certain embodiments of the methods described above, each $R_1$ is hydrogen. In certain embodiments of the methods described above, each $R_1$ is isopropyl.

In certain embodiments of the methods described above, each $R_2$ is independently alkyl or aryl. In certain embodiments of the methods described above, each $R_2$ is independently $C_4$-$C_{14}$ aryl. In certain embodiments of the methods described above, each $R_2$ is independently $C_4$-$C_{10}$ aryl. In certain embodiments of the methods described above, each $R_2$ is independently $C_4$-$C_{14}$ heteroaryl. In certain embodiments of the methods described above, each $R_2$ is independently $C_4$-$C_{10}$ heteroaryl. In certain embodiments of the methods described above, each $R_2$ is independently furanyl, pyridinyl, phenyl, biphenyl, or naphthyl.

In certain embodiments of the methods described above, each $R_2$ is independently lower alkyl. In certain embodiments of the methods described above, each $R_2$ is independently $C_1$-$C_{20}$ alkyl. In certain embodiments of the methods described above, each $R_2$ is independently $C_1$-$C_{10}$ alkyl. In certain embodiments of the methods described above, each $R_2$ is independently $C_1$-$C_5$ alkyl. In certain embodiments of the methods described above, each $R_2$ is independently hydrogen, methyl, or isopropyl. In certain embodiments of the methods described above, each $R_2$ is independently methyl or isopropyl. In certain embodiments of the methods described above, each $R_2$ is methyl. In certain embodiments of the methods described above, each $R_2$ is hydrogen. In certain embodiments of the methods described above, each $R_2$ is isopropyl.

In certain embodiments of the methods described above, each $R_3$ is independently alkyl or aryl. In certain embodiments of the methods described above, each $R_3$ is independently $C_4$-$C_{14}$ aryl. In certain embodiments of the methods described above, each $R_3$ is independently $C_4$-$C_{10}$ aryl. In certain embodiments of the methods described above, each $R_3$ is independently $C_4$-$C_{14}$ heteroaryl. In certain embodiments of the methods described above, each $R_3$ is independently $C_4$-$C_{10}$ heteroaryl. In certain embodiments of the methods described above, each $R_3$ is independently furanyl, pyridinyl, phenyl, biphenyl, or naphthyl.

In certain embodiments of the methods described above, each $R_3$ is independently lower alkyl. In certain embodiments of the methods described above, each $R_3$ is independently $C_1$-$C_{20}$ alkyl. In certain embodiments of the methods described above, each $R_3$ is independently $C_1$-$C_{10}$ alkyl. In certain embodiments of the methods described above, each $R_3$ is independently $C_1$-$C_5$ alkyl. In certain embodiments of the methods described above, each $R_3$ is independently hydrogen, methyl, or isopropyl. In certain embodiments of the methods described above, each $R_3$ is independently methyl or isopropyl. In certain embodiments of the methods described above, each $R_3$ is methyl. In certain embodiments of the methods described above, each $R_3$ is hydrogen. In certain embodiments of the methods described above, each $R_3$ is isopropyl. In certain embodiments of the methods described above, each $R_3$ is cycloalkyl. In certain embodiments of the methods described above, each $R_3$ is $C_3$-$C_{14}$ cycloalkyl. In certain embodiments of the methods described above, each $R_3$ is $C_3$-$C_8$ cycloalkyl.

In certain embodiments of the methods described above, each $R_3$ is independently hydrogen, methyl, or isopropyl. In certain embodiments of the methods described above, each $R_3$ is independently methyl or isopropyl. In certain embodiments of the methods described above, each $R_3$ is methyl. In certain embodiments of the methods described above, each $R_3$ is isopropyl. In certain embodiments of the methods described above, $R_3$ is hydrogen or methyl. In certain embodiments of the methods described above, $R_3$ is hydrogen. In certain embodiments of the methods described above, $R_3$ is methyl.

In certain embodiments of the methods described above, $R_2$ is phenyl, 1-napthyl, 2-methyl-phenyl, 4-methyl-phenyl, trans-Ph-CH=CH, 2-furyl, isobutyl, cyclohexyl, or —C(O)OCH$_2$CH$_3$.

In certain embodiments of the methods described above: $R_1$ is hydrogen, alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is hydrogen, alkyl or aryl. In certain embodiments of the methods described above: $R_1$ is hydrogen, lower alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is hydrogen, lower alkyl or aryl. In certain embodiments of the methods described above: $R_1$ is alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is hydrogen, alkyl or aryl. In certain embodiments of the methods described above: $R_1$ is hydrogen, lower alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is lower alkyl or aryl. In certain embodiments of the methods described above: $R_1$ is hydrogen, alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is lower alkyl or aryl. In certain embodiments of the methods described above: $R_1$ is hydrogen, lower alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is lower alkyl or aryl.

In certain embodiments of the methods described above: $R_1$ is hydrogen; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is hydrogen or methyl.

Compounds

In certain embodiments, provided herein is a compound according to Formula Ia or Ib:

Formula (Ia)

Formula (Ib)

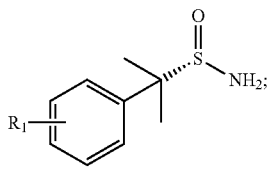

wherein each R₁ is independently hydrogen, alkyl or aryl.

In certain embodiments, provided herein is a compound according to Formula IIa or IIb:

Formula (IIa)

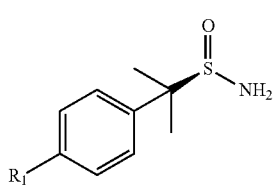

Formula (IIb)

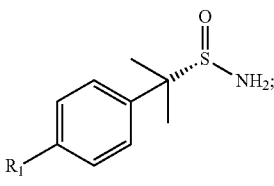

wherein R₁ is as defined in the context of formulas Ia and Ib.

In certain embodiments, provided herein is a substantially diastereomerically pure compound according to any of Formulas Ia, Ib, IIa, or IIb:

Formula (Ia)

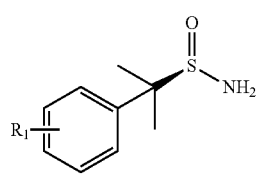

Formula (Ib)

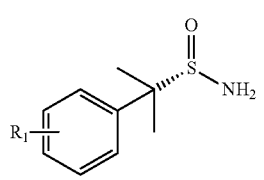

Formula (IIa)

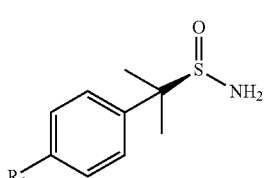

Formula (IIb)

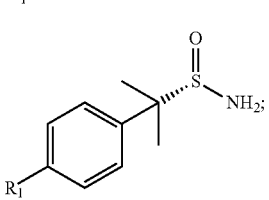

wherein each R₁ is independently hydrogen, alkyl or aryl. In an embodiment, provided herein are compositions comprising a compound of formula Ia which does not comprise a compound of formula Ib. In an embodiment, provided herein are compositions comprising a compound of formula Ib which does not comprise a compound of formula Ia. In an embodiment, provided herein are compositions comprising a compound of formula IIa which does not comprise a compound of formula IIb. In an embodiment, provided herein are compositions comprising a compound of formula IIb which does not comprise a compound of formula IIa.

In an embodiment, a compound of any of formulas Ia, Ib, IIa, or IIb is provided wherein each $R_1$ is independently alkyl or aryl. In an embodiment, a compound of any of formulas Ia, Ib, IIa, or IIb is provided wherein each $R_1$ is independently $C_4$-$C_{14}$ aryl. In an embodiment, a compound of any of formulas Ia, Ib, IIa, or IIb is provided wherein each $R_1$ is independently $C_4$-$C_{10}$ aryl. In an embodiment, a compound of any of formulas Ia, Ib, IIa, or IIb is provided wherein each $R_1$ is independently $C_4$-$C_{14}$ heteroaryl. In an embodiment, a compound of any of formulas Ia, Ib, IIa, or IIb is provided wherein each $R_1$ is independently $C_4$-$C_{10}$ heteroaryl. In an embodiment, a compound of any of formulas Ia, Ib, IIa, or IIb is provided wherein each $R_1$ is independently furanyl, pyridinyl, phenyl, biphenyl, or naphthyl.

In an embodiment, a compound of any of formulas Ia, Ib, IIa, or IIb is provided wherein each $R_1$ is independently lower alkyl. In an embodiment, a compound of any of formulas Ia, Ib, IIa, or IIb is provided wherein each $R_1$ is independently $C_1$-$C_{20}$ alkyl. In an embodiment, a compound of any of formulas Ia, Ib, IIa, or IIb is provided wherein each $R_1$ is independently $C_1$-$C_{10}$ alkyl. In an embodiment, a compound of any of formulas Ia, Ib, IIa, or IIb is provided wherein each $R_1$ is independently $C_1$-$C_5$ alkyl.

In an embodiment, a compound of any of formulas Ia, Ib, IIa, or IIb is provided wherein each $R_1$ is independently hydrogen, methyl, or isopropyl. In an embodiment, a compound of any of formulas Ia, Ib, IIa, or IIb is provided wherein each $R_1$ is independently methyl or isopropyl. In an embodiment, a compound of any of formulas Ia, Ib, IIa, or IIb is provided wherein each $R_1$ is methyl. In an embodiment, a compound of any of formulas Ia, Ib, IIa, or IIb is provided wherein each $R_1$ is isopropyl. In an embodiment, a compound of any of formulas Ia, Ib, IIa, or IIb is provided wherein each $R_1$ is hydrogen.

In certain embodiments, provided herein is a compound according to formula IIIa or IIIb:

Formula (IIIa)

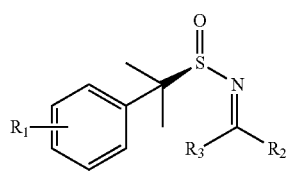

Formula (IIIb)

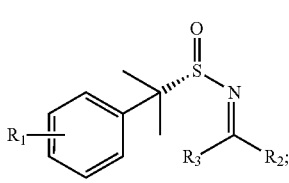

wherein each of $R_1$, $R_2$, and $R_3$ is independently hydrogen, alkyl or aryl.

In certain embodiments, provided herein is a substantially diastereomerically pure compound according to formula IIIa or IIIb:

Formula (IIIa)

[Chemical structure showing R$_1$-substituted phenyl group attached to C(CH$_3$)$_2$ bonded to S(=O)-N=C(R$_3$)(R$_2$)]

Formula (IIIb)

[Chemical structure showing R$_1$-substituted phenyl group attached to C(CH$_3$)$_2$ bonded to S(=O)-N=C(R$_3$)(R$_2$) with opposite stereochemistry]

wherein each of R$_1$, R$_2$, and R$_3$ is independently hydrogen, alkyl or aryl. In an embodiment, provided herein are compositions comprising a compound of formula IIIa which does not comprise a compound of formula IIIb. In an embodiment, provided herein are compositions comprising a compound of formula IIIb which does not comprise a compound of formula IIIa.

In an embodiment, a compound of any of formulas IIIa or IIIb is provided wherein each R$_1$ is independently alkyl or aryl. In an embodiment, a compound of any of formulas IIIa or IIIb is provided wherein each R$_1$ is independently C$_4$-C$_{14}$ aryl. In an embodiment, a compound of any of formulas IIIa or IIIb is provided wherein each R$_1$ is independently C$_4$-C$_{10}$ aryl. In an embodiment, a compound of any of formulas IIIa or IIIb is provided wherein each R$_1$ is independently C$_4$-C$_{14}$ heteroaryl. In an embodiment, a compound of any of formulas IIIa or IIIb is provided wherein each R$_1$ is independently C$_4$-C$_{10}$ heteroaryl. In an embodiment, a compound of any of formulas IIIa or IIIb is provided wherein each R$_1$ is independently furanyl, pyridinyl, phenyl, biphenyl, or naphthyl.

In an embodiment, a compound of any of formulas IIIa or IIIb is provided wherein each R$_1$ is independently lower alkyl. In an embodiment, a compound of any of formulas IIIa or IIIb is provided wherein each R$_1$ is independently C$_1$-C$_{20}$ alkyl. In an embodiment, a compound of any of formulas IIIa or IIIb is provided wherein each R$_1$ is independently C$_1$-C$_{10}$ alkyl. In an embodiment, a compound of any of formulas IIIa or IIIb is provided wherein each R$_1$ is independently C$_1$-C$_5$ alkyl. In an embodiment, a compound of any of formulas IIIa or IIIb is provided wherein each R$_1$ is independently hydrogen, methyl, or isopropyl. In an embodiment, a compound of any of formulas IIIa or IIIb is provided wherein each R$_1$ is independently methyl or isopropyl. In an embodiment, a compound of any of formulas IIIa or IIIb is provided wherein each R$_1$ is methyl. In an embodiment, a compound of any of formulas IIIa or IIIb is provided wherein each R$_1$ is hydrogen. In an embodiment, a compound of any of formulas IIIa or IIIb is provided wherein each R$_1$ is isopropyl.

In an embodiment, a compound of any of formulas IIIa or IIIb is provided wherein each R$_2$ is independently alkyl or aryl. In an embodiment, a compound of any of formulas IIIa or IIIb is provided wherein each R$_2$ is independently C$_4$-C$_{14}$ aryl. In an embodiment, a compound of any of formulas IIIa or IIIb is provided wherein each R$_2$ is independently C$_4$-C$_{10}$ aryl. In an embodiment, a compound of any of formulas IIIa or IIIb is provided wherein each R$_2$ is independently C$_4$-C$_{14}$ heteroaryl. In an embodiment, a compound of any of formulas IIIa or IIIb is provided wherein each R$_2$ is independently C$_4$-C$_{10}$ heteroaryl. In an embodiment, a compound of any of formulas IIIa or IIIb is provided wherein each R$_2$ is independently furanyl, pyridinyl, phenyl, biphenyl, or naphthyl.

In an embodiment, a compound of any of formulas IIIa or IIIb is provided wherein each R$_2$ is independently lower alkyl. In an embodiment, a compound of any of formulas IIIa or IIIb is provided wherein each R$_2$ is independently C$_1$-C$_{20}$ alkyl. In an embodiment, a compound of any of formulas IIIa or IIIb is provided wherein each R$_2$ is independently C$_1$-C$_{10}$ alkyl. In an embodiment, a compound of any of formulas IIIa or IIIb is provided wherein each R$_2$ is independently C$_1$-C$_5$ alkyl. In an embodiment, a compound of any of formulas IIIa or IIIb is provided wherein each R$_2$ is independently hydrogen, methyl, or isopropyl. In an embodiment, a compound of any of formulas IIIa or IIIb is provided wherein each R$_2$ is independently methyl or isopropyl. In an embodiment, a compound of any of formulas IIIa or IIIb is provided wherein each R$_2$ is methyl. In an embodiment, a compound of any of formulas IIIa or IIIb is provided wherein each R$_2$ is hydrogen. In an embodiment, a compound of any of formulas IIIa or IIIb is provided wherein each R$_2$ is isopropyl.

In an embodiment, a compound of any of formulas IIIa or IIIb is provided wherein each R$_3$ is independently alkyl or aryl. In an embodiment, a compound of any of formulas IIIa or IIIb is provided wherein each R$_3$ is independently C$_4$-C$_{14}$ aryl. In an embodiment, a compound of any of formulas IIIa or IIIb is provided wherein each R$_3$ is independently C$_4$-C$_{10}$ aryl. In an embodiment, a compound of any of formulas IIIa or IIIb is provided wherein each R$_3$ is independently C$_4$-C$_{14}$ heteroaryl. In an embodiment, a compound of any of formulas IIIa or IIIb is provided wherein each R$_3$ is independently C$_4$-C$_{10}$ heteroaryl. In an embodiment, a compound of any of formulas IIIa or IIIb is provided wherein each R$_3$ is independently furanyl, pyridinyl, phenyl, biphenyl, or naphthyl.

In an embodiment, a compound of any of formulas IIIa or IIIb is provided wherein each R$_3$ is independently lower alkyl. In an embodiment, a compound of any of formulas IIIa or IIIb is provided wherein each R$_3$ is independently C$_1$-C$_{20}$ alkyl. In an embodiment, a compound of any of formulas IIIa or IIIb is provided wherein each R$_3$ is independently C$_1$-C$_{10}$ alkyl. In an embodiment, a compound of any of formulas IIIa or IIIb is provided wherein each R$_3$ is independently C$_1$-C$_5$ alkyl. In an embodiment, a compound of any of formulas IIIa or IIIb is provided wherein each R$_3$ is independently hydrogen, methyl, or isopropyl. In an embodiment, a compound of any of formulas IIIa or IIIb is provided wherein each R$_3$ is independently methyl or isopropyl. In an embodiment, a compound of any of formulas IIIa or IIIb is provided wherein each R$_3$ is methyl. In an embodiment, a compound of any of formulas IIIa or IIIb is provided wherein each R$_3$ is hydrogen. In an embodiment, a compound of any of formulas IIIa or IIIb is provided wherein each R$_3$ is isopropyl. In an embodiment, a compound of any of formulas IIIa or IIIb is provided wherein each R$_3$ is cycloalkyl. In an embodiment, a compound of any of formulas IIIa or IIIb is provided wherein each R$_3$ is C$_3$-C$_{14}$ cycloalkyl. In an embodiment, a compound of any of formulas IIIa or IIIb is provided wherein each R$_3$ is C$_3$-C$_8$ cycloalkyl.

In an embodiment, a compound of any of formulas IIIa or IIIb is provided wherein each R$_3$ is independently hydrogen, methyl, or isopropyl. In an embodiment, a compound of any of formulas IIIa or IIIb is provided wherein each R$_3$ is independently methyl or isopropyl. In an embodiment, a compound of any of formulas IIIa or IIIb is provided wherein each R$_3$ is methyl. In an embodiment, a compound of any of formulas IIIa or IIIb is provided wherein each R$_3$ is isopropyl. In an embodiment, a compound of any of formulas IIIa or IIIb is provided wherein R$_3$ is hydrogen or methyl. In an embodiment, a compound of any of formulas IIIa or IIIb is provided wherein $R_3$ is hydrogen. In an embodiment, a compound of any of formulas IIIa or IIIb is provided wherein $R_3$ is methyl.

In an embodiment, a compound of any of formulas IIIa or IIIb is provided wherein $R_2$ is phenyl, 1-napthyl, 2-methyl-phenyl, 4-methyl-phenyl, trans-Ph-CH=CH, 2-furyl, isobutyl, cyclohexyl, or —C(O)OCH$_2$CH$_3$.

In an embodiment, a compound of any of formulas IIIa or IIIb is provided wherein: $R_1$ is hydrogen, alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is hydrogen, alkyl or aryl. In an embodiment, a compound of any of formulas IIIa or IIIb is provided wherein: $R_1$ is hydrogen, lower alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is hydrogen, lower alkyl or aryl. In an embodiment, a compound of any of formulas IIIa or IIIb is provided wherein: $R_1$ is alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is hydrogen, alkyl or aryl. In an embodiment, a compound of any of formulas IIIa or IIIb is provided wherein: $R_1$ is hydrogen, lower alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is lower alkyl or aryl. In an embodiment, a compound of any of formulas IIIa or IIIb is provided wherein: $R_1$ is hydrogen, alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is lower alkyl or aryl. In an embodiment, a compound of any of formulas IIIa or IIIb is provided wherein: $R_1$ is hydrogen, lower alkyl or aryl; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is lower alkyl or aryl.

In an embodiment, a compound of any of formulas IIIa or IIIb is provided wherein: $R_1$ is hydrogen; $R_2$ is phenyl, 1-napthyl, 2-methyl-phenyl, 4-methyl-phenyl, trans-Ph-CH=CH—, 2-furyl, isobutyl, cyclohexyl, or —C(O)OCH$_2$CH$_3$; and $R_3$ is hydrogen or methyl.

In some embodiments, provided herein is processes for the preparation of compounds as described herein, e.g., of Formula Ia, Ib, IIa, IIb, IIIa, or IIIb, as described in more detail elsewhere herein.

Optically Active Compounds

It is appreciated that compounds provided herein have several chiral centers and are prepared or isolated in optically active forms, for example diastereomerically pure forms. Some compounds may exhibit polymorphism. It is well known in the art how to prepare optically active forms of the diastereomerically pure compounds provided herein, for example, by resolution of the racemic form by recrystallization techniques, by synthesis from optically-active starting materials, by chiral synthesis, or by chromatographic separation using a chiral stationary phase, such as high-performance liquid chromatography.

Diastereomerically pure sulfinamide and imine compounds and purified compositions comprising the diastereomerically pure sulfinamide and imine compounds can be prepared according to techniques known to those of skill in the art. Examples of methods to obtain diastereomerically pure materials are known in the art, and include at least the following:

a) physical separation of crystals—a technique whereby macroscopic crystals of the individual enantiomers are manually separated. This technique can be used if crystals of the separate enantiomers exist, i.e., the material is a conglomerate, and the crystals are visually distinct;

b) simultaneous crystallization—a technique whereby the individual enantiomers are separately crystallized from a solution of the racemate, possible only if the latter is a conglomerate in the solid state;

c) enzymatic resolutions—a technique whereby partial or complete separation of a racemate by virtue of differing rates of reaction for the enantiomers with an enzyme;

d) enzymatic asymmetric synthesis—a synthetic technique whereby at least one step of the synthesis uses an enzymatic reaction to obtain an enantiomerically pure or enriched synthetic precursor of the desired enantiomer;

e) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

f) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

g) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

h) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

i) enantiospecific synthesis from non-racemic precursors—a synthetic technique whereby the desired enantiomer is obtained from non-chiral starting materials and where the stereochemical integrity is not or is only minimally compromised over the course of the synthesis;

j) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

k) chiral gas chromatography—a technique whereby the racemate is volatilized and enantiomers are separated by virtue of their differing interactions in the gaseous mobile phase with a column containing a fixed non-racemic chiral adsorbent phase;

l) extraction with chiral solvents—a technique whereby the enantiomers are separated by virtue of preferential dissolution of one enantiomer into a particular chiral solvent;

m) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, provided are compositions of diastereomerically pure sulfinamide and imine compounds that are substantially free of a designated diastereomer of that compound. In certain embodiments, in the methods and compounds of this invention, the compounds are substantially free of other diastereomers. In some embodiments, a composition includes a compound that is at least 85%, 90%, 95%, 98%, 99% or 100% by weight, of the compound, the remainder comprising other chemical species or diastereomers.

Isotopically Enriched Compounds

Also provided herein are isotopically enriched compounds, including but not limited to isotopically enriched diastereomerically pure sulfinamide and imine compounds.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

Preparation of Compounds

The compounds provided herein can be prepared, isolated or obtained by any method apparent to those of skill in the art. Exemplary methods of preparation are described in detail in the examples below. In certain embodiments, compounds provided herein can be prepared according to Exemplary Preparation Schemes 1a and 1b, as discussed further below.

Exemplary Preparation Scheme 1a

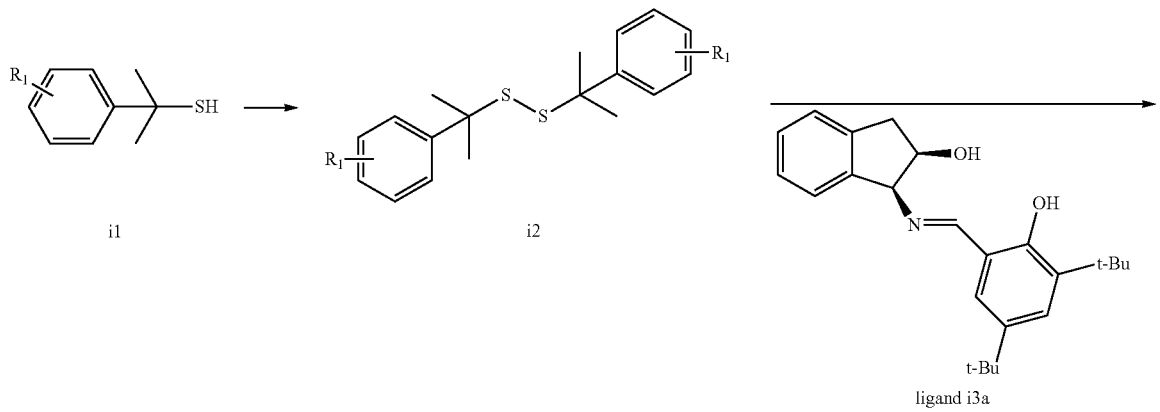

i1 i2 ligand i3a

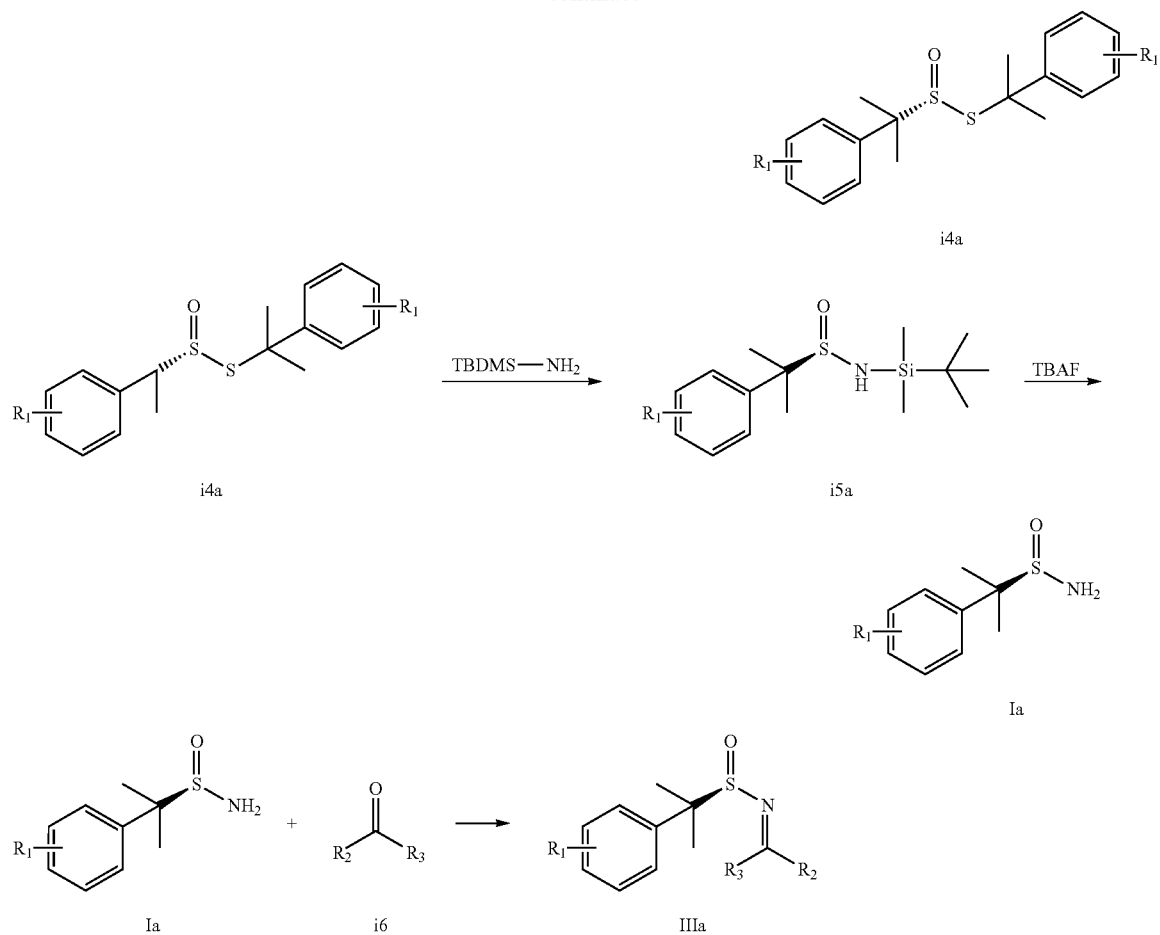
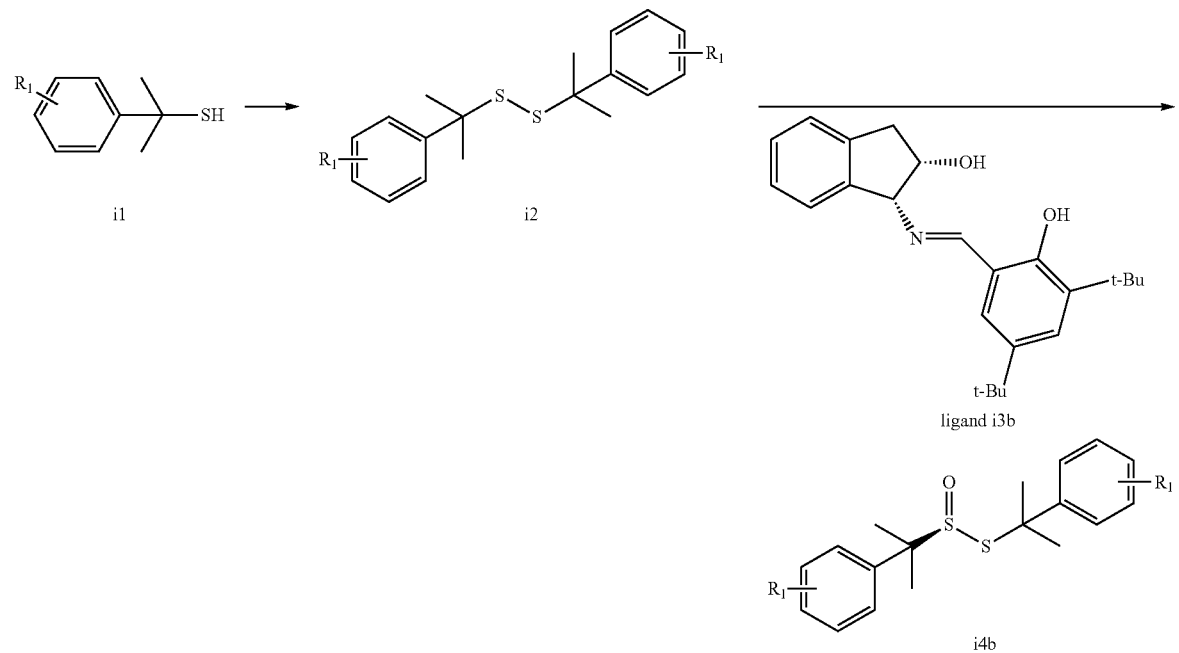
Exemplary Preparation Scheme 1b

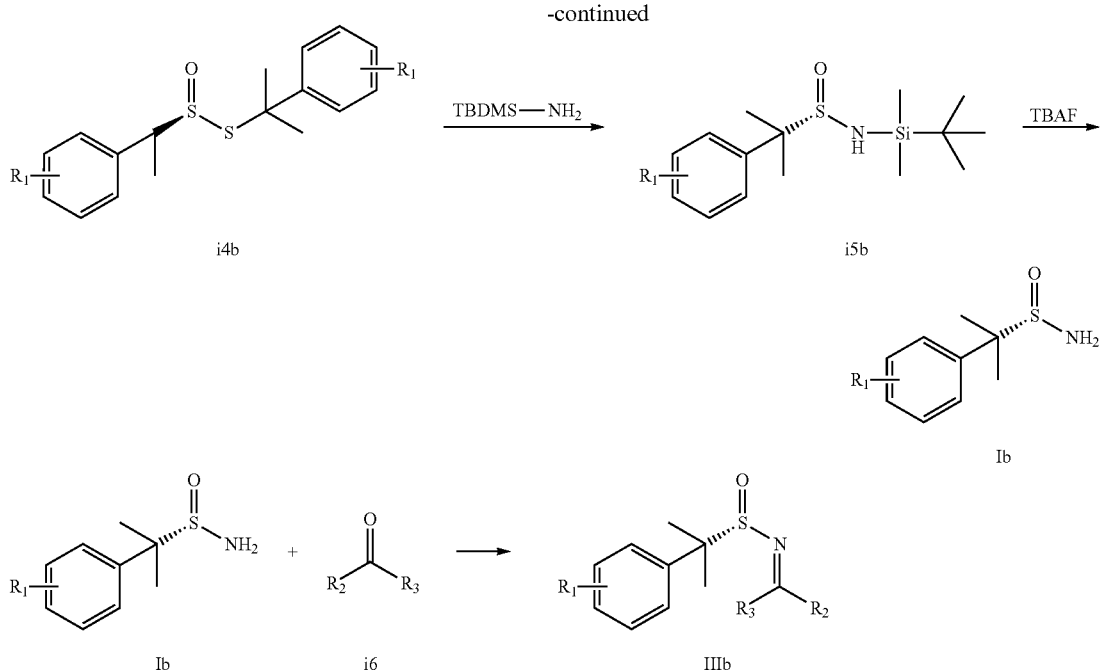

In certain embodiments, one or more protection or deprotection steps may be included in the methods of preparation described in Exemplary Preparation Schemes 1a and 1b. In certain embodiments, provided herein is a compound prepared according to the above Exemplary Preparation Scheme 1a or 1b.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography or high performance liquid chromatography); THF (tetrahydrofuran); $CDCl_3$ (deuterated chloroform); AcOH (acetic acid); DCM (dichloromethane); DMSO (dimethylsulfoxide); DMSO-$d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

The Examples below provide methods of synthesis of ($R_S$)-2-phenylpropyl-2-sulfinamides and ($S_S$)-2-phenylpropyl-2-sulfinamides. Also provided are methods of synthesis of other sulfinamides, such as ($R_S$)-2-arylpropyl-2-sulfinamides. In addition, provided are methods to synthesize sulfonamides from thiosulfinates, wherein the thiosulfinates have aromatic groups. Also provided are methods using TBDMS-$NH_2$ as a nitrogen source to provide chiral sulfinamides from chiral thiosulfinates without racemization or side products. Also provided are methods for the preparation of ($R_S$)-2-phenylpropyl-2-sulfinylimines from free sulfinamides.

ABBREVIATIONS

TBDMS is tert-butyldimethylsilyl. TBAF is tetra-n-butylammonium fluoride. HPLC is high-performance liquid chromatography. THF is tetrahydrofuran. Ph is phenyl. M.S. is molecular sieve.

Example 1

Synthesis of ($R_S$)-2-phenylpropyl-2-sulfinamide

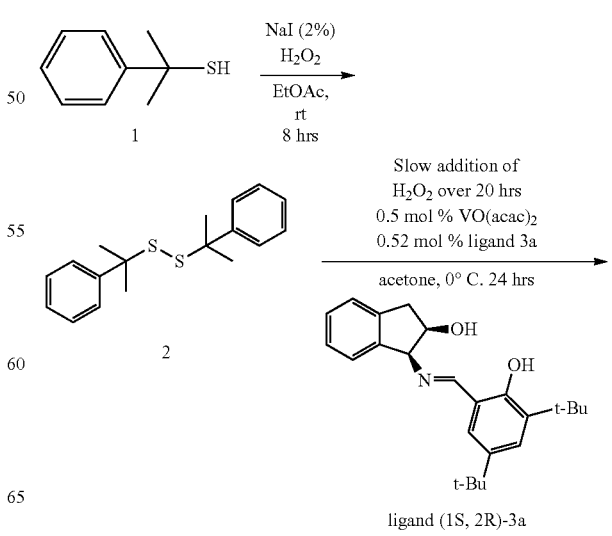

Scheme 1

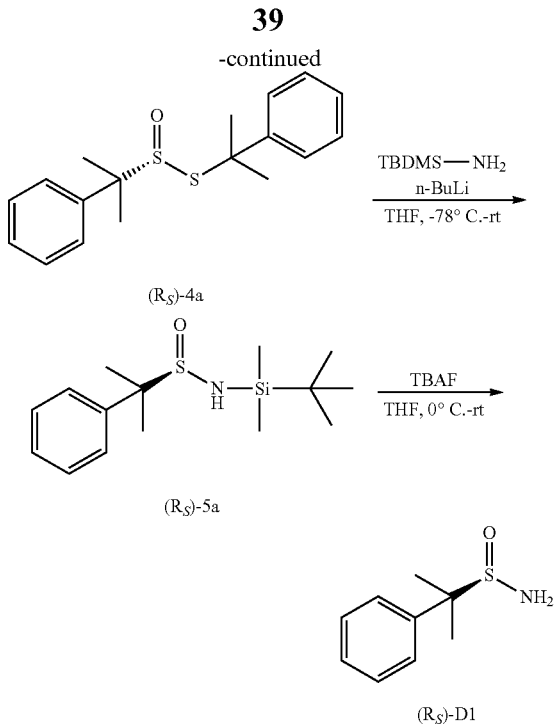

($R_S$)-2-phenylpropyl-2-sulfinamides were synthesized starting from thiol 1. As shown in the scheme 1, thiol 1 was converted into disulfide 2, which was then oxidized in presence of commercially available chiral ligand (1S,2R)-3a to produce ($R_S$)-thiosulfinate ($R_S$)-4a. The chiral thiosulfinate ($R_S$)-4a was converted to TBDMS protected sulfinamide ($R_S$)-5a with TBDMS-NH$_2$. The final deprotection of TBDMS yielded the desired ($R_S$)-2-phenylpropyl-2-sulfinamide ($R_S$)-D1 with good overall yields.

1.1. Synthesis of Disulfide 2

To a stirred solution of thiol 1 (78.8 mmol) in 240 mL of ethyl acetate was added NaI (236 mg, 1.57 mmol), and to this reaction mixture 30% aq.H$_2$O$_2$ (8.9 mL, 78.8 mmol) was added slowly at room temperature. Reaction mixture was stirred at room temperature for 18 hours. At this stage, saturated aq. Na$_2$S$_2$O$_3$ was added, and the mixture was extracted with ethyl acetate. The resulting organic layer was dried over anhydrous Na$_2$SO$_4$ and evaporated under reduced pressure. The crude mixture was purified by column chromatography with pure hexanes as eluant to give 9.29 g (78%) of disulfide 2.

$^1$H NMR (CDCl$_3$, 400 MHz): δ=1.75 (s, 12H), 7.42-7.44 (m, 2H), 7.49-7.54 (m, 4H), 7.67-7.69 (m, 4H). $^{13}$C NMR (CDCl$_3$, 100 MHz): δ=29.5, 52.2, 127.1, 127.4, 128.4, 128.5, 145.9.

1.2. Synthesis of Thiosulfinate ($R_S$)-4a

A 100 mL Schlenk flask was loaded with ligand ($S_S$)-3a (62.8 mg, 0.1719 mmol) and vanadyl acetylacetanoate (44 mg, 0.165 mmol). Acetone (20 mL) was added and stirred the resulting dark-green solution at room temperature for 30 minutes, while open to the air. To this solution, disulfide 2 (10 g, 33.05 mmol) was added. The resulting mixture was cooled to 0° C. and 30% aq. H$_2$O$_2$ was added slowly with syringe pump over 20 hours. The dark-brown color solution was stirred for another 26 hours at 0° C. The reaction was quenched with saturated aq. Na$_2$S$_2$O$_3$, the resulting mixture was extracted with ethyl acetate. The combined organic layers were washed with brine and dried over anhydrous Na$_2$SO$_4$. The organic layer was evaporated under reduced pressure to afford crude ($R_S$)-thiosulfinate ($R_S$)-4a as white solid, which was washed with hexanes to provide 7.9 g (75%) of pure ($R_S$)-thiosulfinate ($R_S$)-4a with 85% ee. The enantiomeric excess was further improved to 94% by washing with hexanes (10 mL of hexanes required for 1 g of thiosulfinate). HPLC, Daicel ChiralPak AS-H column, 98:2 Hexanes/$^i$PrOH; 1.0 mL/min, 230 nm, t$_R$=14.7 min; t$_S$=19.1 min; [α]$_D^{25}$=+126.2° (c=1.0, CHCl$_3$); $^1$H NMR (CDCl$_3$, 400 MHz): δ=1.63 (s, 3H), 1.77-1.82 (m, 9H), 7.24-7.41 (m, 1H). $^{13}$C NMR (CDCl$_3$, 100 MHz): δ=21.8, 24.4, 31.0, 31.9, 53.3, 65.5, 126.6, 126.7, 127.4, 128.1, 128.3, 128.4, 139.8, 145.1.

1.3. Synthesis of TBDMS Protected Sulfinamide ($R_S$)-5a

TBDMS-NH$_2$ was prepared from TBDMS-Cl by a known literature method. Urgaonkar, S.; Cortese, J. F.; Barker, R. H.; Cornwell, M.; Serrano, A. E.; Wirth, D. F.; Clardy, J.; Mazitschek, R. Org. Lett. 2010, 12, 3998. Freshly synthesized 1M solution of TBDMS-NH$_2$ (35.1 mL, 35.1 mmol) in THF was taken in a dry round bottomed flask under argon. To this solution, 1.6 M n-BuLi (22.0 mL, 35.16 mmol) was added drop wise at −78° C., and the mixture was stirred at the same temperature. After 30 minutes the pre dissolved solution of thiosulfinate ($R_S$)-4a (2.8 g, 8.79 mmol) in THF was added slowly at −78° C. The reaction temperature raised to room temperature slowly, and stirred until the starting material consumed, monitored by TLC. At this stage, reaction quenched with 1 mL aq. NH$_4$Cl solution, and extracted with ethyl acetate. The organic layer was dried over anhydrous Na$_2$SO$_4$, and evaporated under reduced pressure to afford crude TBDMS protected sulfinamide ($R_S$)-5a. The crude product was purified by column chromatography to get 2.45 g (93%) of compound ($R_S$)-5a as white solid with 94% ee. HPLC, AS-H column, 93:7 Hexanes/$^i$PrOH; 1.0 mL/min, 254 nm, t$_S$=4.8 min; t$_R$=7.2 min; [α]$_D^{25}$=−31.8° (c=1.0, CHCl$_3$); $^1$H NMR (CDCl$_3$, 400 MHz): δ=0.02 (d, J=10.1 Hz, 6H), 0.76 (s, 9H), 1.52 (s, 3H), 1.65 (s, 3H), 2.48 (br, 1H), 7.28-7.34 (m, 1H), 7.35-7.40 (m, 3H). $^{13}$C NMR (CDCl$_3$, 100 MHz): δ=−4.7, −4.2, 17.5, 22.0, 22.4, 25.5, 62.8, 127.7, 127.8, 128.2, 136.7.

1.4. Synthesis of Sulfinamide ($R_S$)-D1

A dry round bottom flask was charged with TBDMS protected sulfinamide ($R_S$)-5a (1.32 g, 4.44), and THF (23 mL) under argon and was added TBAF (5.33 mL, 5.33 mmol) at 0° C. After 1 hour, TLC indicated that all starting material was consumed. Then the reaction was quenched with 1 mL of water and extracted with ethyl acetate. The organic layer was dried over anhydrous Na$_2$SO$_4$, and evaporated under reduced pressure to afford crude sulfinamide ($R_S$)-D1. The crude product was purified by column chromatography with ethyl acetate as eluant to afford pure sulfinamide ($R_S$)-D1 0.8 g (98%) with 94% ee. HPLC, OD-H column, 93:7 Hexanes/$^i$PrOH; 1.0 mL/min, 254 nm, t$_R$=21.0 min; t$_S$=24.9 min; [α]$_D^{25}$=−100.2° (c=1.0, CHCl$_3$); $^1$H NMR (CDCl$_3$, 400 MHz): δ=1.52 (s, 3H), 1.60 (s, 3H), 3.69 (br, 2H) 7.24-7.27 (m, 1H), 7.31-7.39 (m, 4H). $^{13}$C NMR (CDCl$_3$, 100 MHz): δ=21.7, 22.5, 61.0, 127.3, 127.5, 127.7, 136.5.

1.5. Synthesis of ($S_S$) Sulfinamides ($S_S$)-D1

Scheme 4

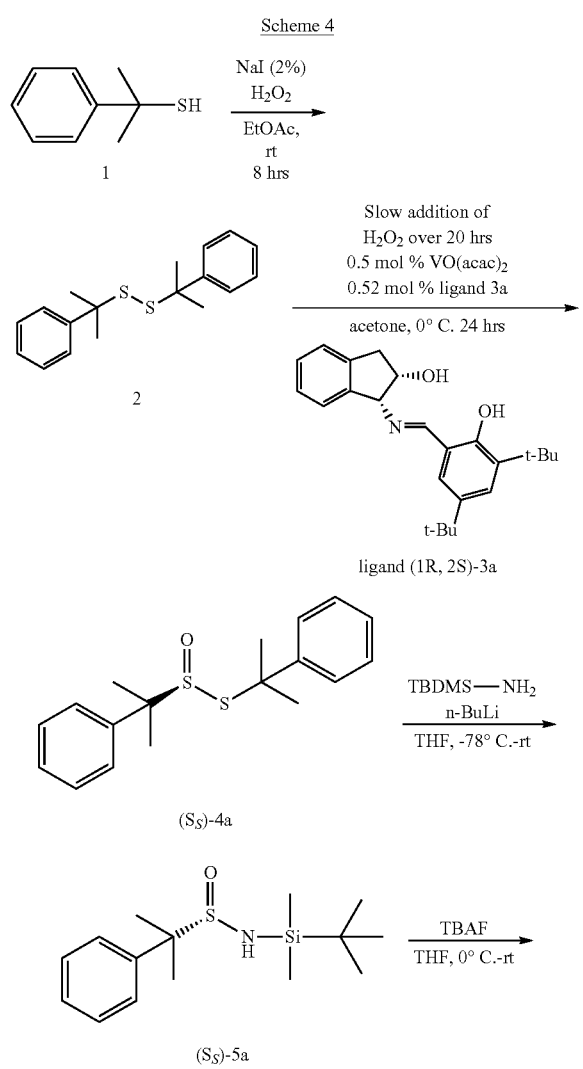

($S_S$)-4a ($S_S$)-5a ($S_S$)-D1

As shown in Scheme 4, using organocatalysis, commercially available ligand (1R,2S)-3a (((1R,2S)-1-[(3,5-Di-tert-butyl-2-hydroxybenzylidene)amino]-2-indanol) produces the ($S_S$)-thiosulfinate ($S_S$)-4a, which is an enantiomer of ($R_S$)-4a. Subsequently, ($S_S$)-sulfinamides ($S_S$)-D1 and their imines are synthesized using the same protocols shown in Scheme 1 and Scheme 3.

Absolute stereochemistry was determined from the X-ray structure of the nucleophilic addition product, not shown. Stereochemistry of the products was confirmed from the rotation value. Stereochemical purity was determined by HPLC.

Example 2

General Procedure for the Synthesis of ($R_S$)-2-Phenylpropyl-2-Sulfinylimines Scheme 2

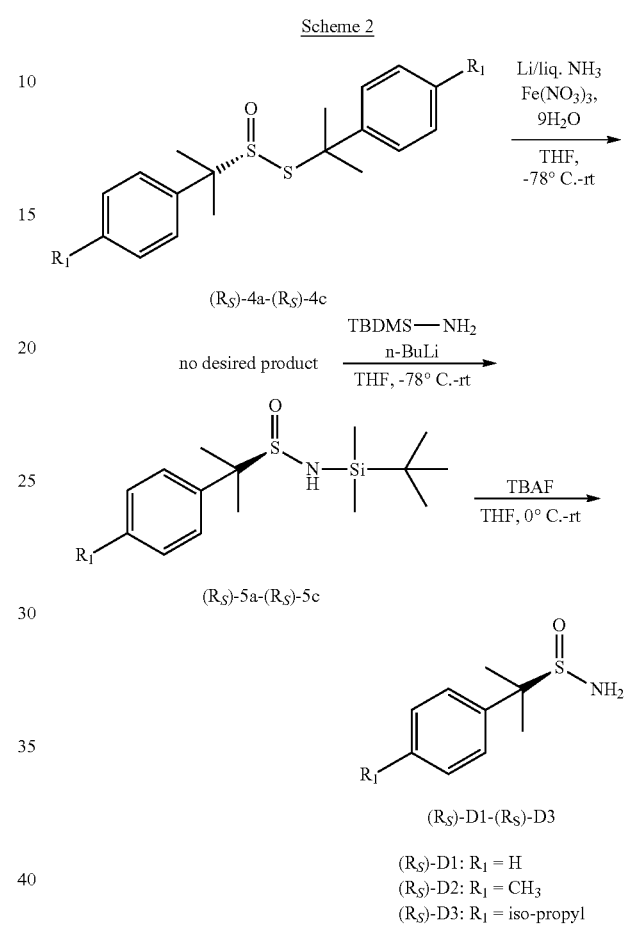

($R_S$)-4a-($R_S$)-4c ($R_S$)-5a-($R_S$)-5c ($R_S$)-D1-($R_S$)-D3

($R_S$)-D1: $R_1$ = H
($R_S$)-D2: $R_1$ = $CH_3$
($R_S$)-D3: $R_1$ = iso-propyl

Scheme 3

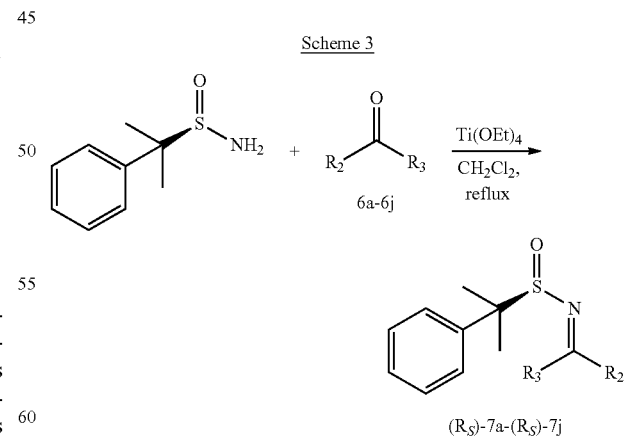

($R_S$)-7a-($R_S$)-7j

To a stirred solution of sulfinamide ($R_S$)-D1 (150 mg, 0.818 mmol), in freshly distilled dichloromethane (20 mL), was added respective aldehyde (1.636 mmol), Ti(OEt)$_4$ (1.22 mL, 5.81 mmol) under argon. The flask was fitted with condenser and refluxed the reaction for 12-16 hours. Then the reaction was quenched with water (5 mL), and the precipitate was filtered through celite pad. The filter cake was washed with dichloromethane, and the filtrate was extracted with the same. The organic layer was dried over anhydrous $Na_2SO_4$, and evaporated under reduced pressure to afford crude sulfinylimine. The crude product was purified by column chromatography and hexanes, ethyl acetate mixture (4:1) was used as an eluant mixture to get corresponding sulfinylimines. In case of glyoxylate 6i, for the synthesis of its imine M.S. (4 Å) was used instead of $Ti(OEt)_4$. Results are provided in Table 1.

Absolute stereochemistry was determined from the X-ray structure of the nucleophilic addition product, not shown. Stereochemistry of the products was confirmed from the rotation value. Stereochemical purity was determined by HPLC.

Compound $(R_S)$-7a: $[\alpha]_D^{25}=+17.7°$ (c=1.0, $CHCl_3$); $^1H$ NMR ($CDCl_3$, 400 MHz): δ=1.69 (s, 3H), 1.75 (s, 3H), 7.22-7.31 (m, 3H), 7.37-7.46 (m, 5H), 7.65-7.68 (m, 2H), 8.29 (s, 1H). $^{13}C$ NMR ($CDCl_3$, 100 MHz): δ=21.1, 21.8, 64.4, 127.3, 127.5, 127.8, 128.7, 129.1, 132.2, 133.8, 138.1, 162.6.

Compound $(R_S)$-7b: $[\alpha]_D^{25}=+34.5°$ (c=1.0, $CHCl_3$); $^1H$ NMR ($CDCl_3$, 400 MHz): δ=1.68 (s, 3H), 1.82 (s, 3H), 7.22-7.35 (m, 3H), 7.45-7.53 (m, 5H), 7.82-7.86 (m, 2H), 7.96 (d, J=8.2 Hz, 1H), 8.70-8.73 (m, 1H), 8.82 (s, 1H). $^{13}C$ NMR ($CDCl_3$, 100 MHz): δ=19.9, 22.6, 64.4, 124.7, 125.0, 126.3, 127.3, 127.6, 127.8, 128.0, 128.6, 129.1, 130.9, 132.5, 133.3, 133.7, 138.6, 162.8.

Compound $(R_S)$-7c: $[\alpha]_D^{25}=-53.9°$ (c=1.0, $CHCl_3$); $^1H$ NMR ($CDCl_3$, 400 MHz): δ=1.68 (s, 3H), 1.74 (s, 3H), 2.37 (s, 3H), 7.15-7.17 (m, 2H), 7.21-7.24 (m, 2H), 7.27-7.33 (m, 3H), 7.37-7.40 (m, 2H), 7.71-7.73 (m, 1H), 8.49 (s, 1H). $^{13}C$ NMR ($CDCl_3$, 100 MHz): δ=19.6, 21.2, 21.9, 64.3, 126.1, 127.4, 127.5, 127.8, 129.2, 131.1, 131.9, 161.6.

Compound $(R_S)$-7d: $[\alpha]_D^{25}=+58.3°$ (c=1.0, $CHCl_3$); $^1H$ NMR ($CDCl_3$, 400 MHz): δ=1.73 (s, 3H), 1.79 (s, 3H), 2.43 (s, 3H), 7.25-7.29 (m, 3H), 7.33-7.37 (m, 2H), 7.43-7.46 (m, 2H), 7.61-7.63 (m, 2H), 8.26 (s, 1H). $^{13}C$ NMR ($CDCl_3$, 100 MHz): δ=21.1, 21.6, 21.8, 64.3, 127.4, 127.5, 127.8, 129.2, 129.4, 131.4, 138.2, 143.0, 162.4.

Compound $(R_S)$-7e: $[\alpha]_D^{25}=-219.7°$ (c=1.0, $CHCl_3$); $^1H$ NMR ($CDCl_3$, 400 MHz): δ=1.73 (s, 3H), 1.78 (s, 3H), 6.96-7.03 (m, 1H), 7.09-7.13 (m, 1H), 7.31-7.37 (m, 1H), 7.40-7.54 (m, 9H), 8.11 (d, J=9.2 Hz, 1H). $^{13}C$ NMR ($CDCl_3$, 100 MHz): δ=20.9, 21.8, 64.2, 125.2, 127.2, 127.5, 127.7, 127.8, 128.7, 130.0, 134.7, 138.1, 146.2, 163.6.

Compound $(R_S)$-7f: $[\alpha]_D^{25}=+105.8°$ (c=1.0, $CHCl_3$); $^1H$ NMR ($CDCl_3$, 400 MHz): δ=1.70 (s, 6H), 6.49-6.50 (m, 1H), 6.83-6.84 (m, 1H), 7.22-7.30 (m, 3H), 7.36-7.38 (m, 2H), 7.57-7.58 (m, 1H), 7.99 (s, 1H). $^{13}C$ NMR ($CDCl_3$, 100 MHz): δ=21.2, 21.9, 64.7, 112.3, 118.6, 127.5, 127.6, 127.8, 137.7, 146.7, 149.6, 150.6.

Compound $(R_S)$-7 g: $[\alpha]_D^{25}=-230.5°$ (c=1.0, $CHCl_3$); $^1H$ NMR ($CDCl_3$, 400 MHz): δ=0.88 (t, J=6.4 Hz, 6H), 1.73 (s, 3H), 1.74 (s, 3H), 1.81-1.91 (m, 1H), 2.16-2.21 (m, 2H), 7.31-7.33 (m, 1H), 7.35-7.41 (m, 4H), 7.72 (t, J=5.5 Hz, 1H). $^{13}C$ NMR ($CDCl_3$, 100 MHz): δ=21.6, 21.8, 22.3, 22.5, 25.9, 44.6, 63.1, 127.3, 127.5, 127.8, 137.9, 169.5.

Compound $(R_S)$-7h: $[\alpha]_D^{25}=-197.0°$ (c=1.0, $CHCl_3$); $^1H$ NMR ($CDCl_3$, 400 MHz): δ=1.04-1.27 (m, 6H), 1.62-1.72 (m, 10H), 2.17-2.21 (m, 1H), 7.27-7.31 (m, 1H), 7.32-7.39 (m, 4H), 7.57 (d, J=4.6 Hz, 1H). $^{13}C$ NMR ($CDCl_3$, 100 MHz): δ=21.5, 22.1, 25.2, 25.7, 28.7, 28.8, 43.8, 63.1, 127.4, 127.5, 127.7, 137.8, 172.6.

Compound $(R_S)$-7i: $[\alpha]_D^{25}=-127.0°$ (c=1.0, $CHCl_3$); $^1H$ NMR ($CDCl_3$, 400 MHz): δ=1.29 (t, J=7.3 Hz, 3H), 1.72 (d, J=3.2 Hz, 6H), 4.25-4.28 (m, 2H), 7.25-7.32 (m, 5H), 7.51 (d, 1H). $^{13}C$ NMR ($CDCl_3$, 100 MHz): δ=14.0, 21.4, 22.7, 62.2, 65.9, 127.4, 127.9, 128.1, 136.6, 155.1, 160.8.

Compound $(R_S)$-7j: $[\alpha]_D^{25}=-223.6°$ (c=1.0, $CHCl_3$); $^1H$ NMR ($CDCl_3$, 400 MHz): δ=1.76 (s, 3H), 1.78 (s, 3H), 2.16 (s, 3H), 7.21-7.37 (m, 5H), 7.41-7.43 (m, 3H), 7.69 (d, J=7.8 Hz, 2H). $^{13}C$ NMR ($CDCl_3$, 100 MHz): δ=18.6, 19.4, 22.9, 64.5, 127.2, 127.6, 127.6, 128.1, 128.3, 131.5, 138.2, 139.2, 176.2.

TABLE 1

Results of N-($R_S$)-2-phenylpropyl-2-sulfinylimines

| Entry | Aldehyde or ketone | $R_2$ | $R_3$ | Product | Yield (%) |
|---|---|---|---|---|---|
| 1 | 6a | phenyl | H | $(R_S)$-7a | 98 |
| 2 | 6b | 1-naphthyl | H | $(R_S)$-7b | 97 |
| 3 | 6c | 2-Me-phenyl | H | $(R_S)$-7c | 89 |
| 4 | 6d | 4-Me-phenyl | H | $(R_S)$-7d | 96 |
| 5 | 6e | trans-PhCH=CH | H | $(R_S)$-7e | 92 |
| 6 | 6f | 2-furyl | H | $(R_S)$-7f | 92 |
| 7 | 6g | iso-butyl | H | $(R_S)$-7g | 87 |
| 8 | 6h | cyclohexyl | H | $(R_S)$-7h | 88 |
| 9 | 6i | —COOEt | H | $(R_S)$-7i | 45 |
| 10 | 6j | phenyl | Me | $(R_S)$-7j | 52 |

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A compound according to Formula Ia or Ib:

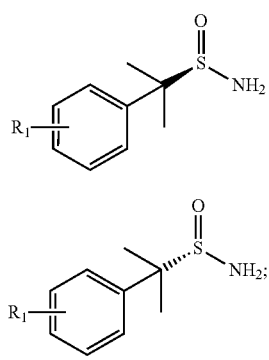

Formula (Ia)

Formula (Ib)

wherein each $R_1$ is independently hydrogen, alkyl or aryl.

2. The compound of claim 1 according to Formula IIa or IIb:

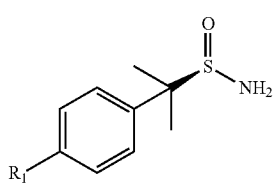

Formula (IIa)

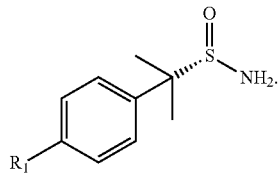

Formula (IIb)

3. A compound according to formula IIIa or IIIb:

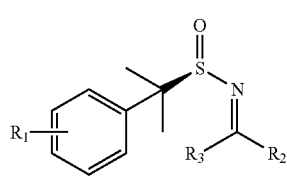

Formula (IIIa)

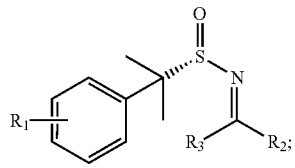

Formula (IIIb)

wherein each of $R_1$, $R_2$, and $R_3$ is independently hydrogen, alkyl or aryl.

4. A method for preparing a compound of Formula Ia, the method comprising:

a. reacting a compound of formula i2 in the presence of a compound of formula i3a to form a compound of formula i4a:

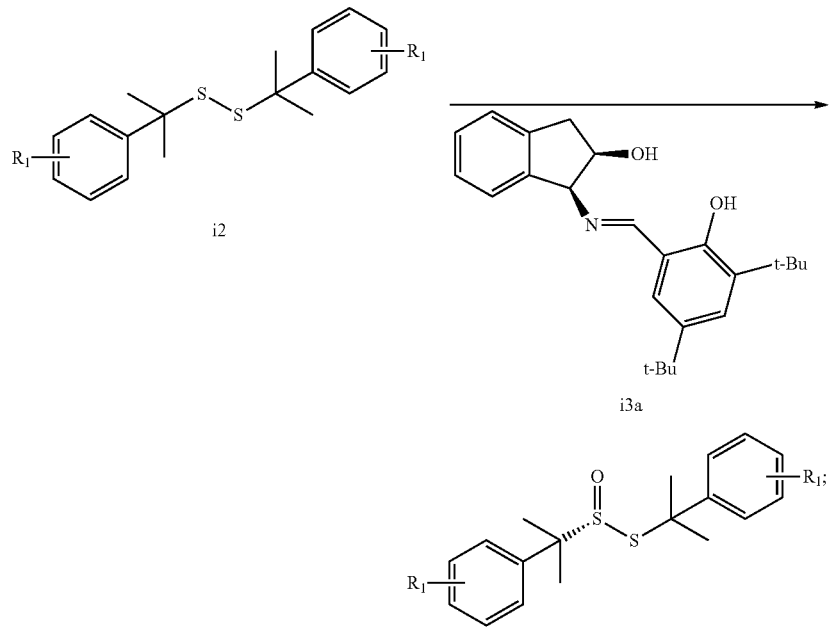

b. reacting the compound of formula i4a in the presence of TBDMS-NH$_2$ to form a compound of formula i5a:
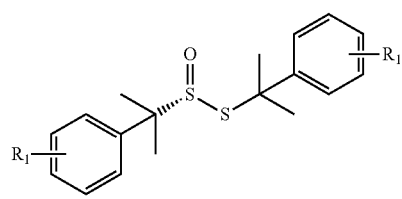
i4a
and
c. reacting the compound of formula i5a in the presence of TBAF to form the compound of formula Ia:
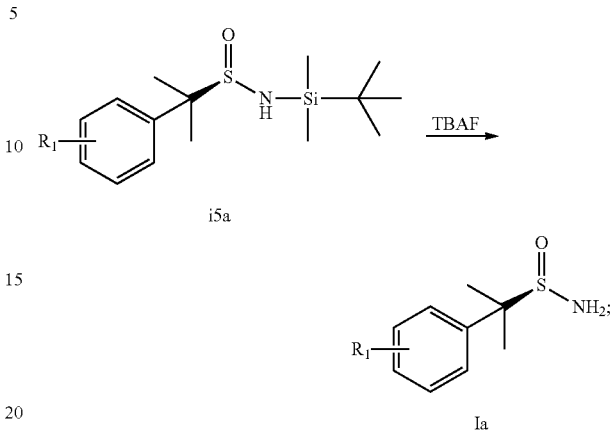
wherein each R$_1$ is independently hydrogen, alkyl or aryl.
* * * * *